(12) United States Patent
Gjerde

(10) Patent No.: US 9,637,719 B2
(45) Date of Patent: May 2, 2017

(54) DEVICES AND METHODS FOR PURIFICATION OF BIOLOGICAL CELLS

(71) Applicant: Douglas T. Gjerde, Saratoga, CA (US)

(72) Inventor: Douglas T. Gjerde, Saratoga, CA (US)

(73) Assignee: Douglas T. Gjerde, Saratoga, CA (US)

( * ) Notice: Subject to any disclaimer, the term of this patent is extended or adjusted under 35 U.S.C. 154(b) by 88 days.

(21) Appl. No.: 14/563,994

(22) Filed: Dec. 8, 2014

(65) Prior Publication Data
US 2015/0240229 A1  Aug. 27, 2015

Related U.S. Application Data

(60) Provisional application No. 61/913,190, filed on Dec. 6, 2013.

(51) Int. Cl.
| | | |
|---|---|---|
| *C12N 11/06* | (2006.01) | |
| *C12N 1/02* | (2006.01) | |
| *C12N 5/00* | (2006.01) | |
| *C12N 5/076* | (2010.01) | |
| *C12N 5/0789* | (2010.01) | |
| *C12N 5/09* | (2010.01) | |
| *C12M 1/00* | (2006.01) | |

(52) U.S. Cl.
CPC ............... *C12N 1/02* (2013.01); *C12M 47/02* (2013.01); *C12N 5/0081* (2013.01); *C12N 5/061* (2013.01); *C12N 5/0647* (2013.01); *C12N 5/0693* (2013.01)

(58) Field of Classification Search
None
See application file for complete search history.

(56) References Cited

U.S. PATENT DOCUMENTS

| | | | | |
|---|---|---|---|---|
| 5,693,223 A | * | 12/1997 | Yamada | B01D 15/08 210/198.2 |
| 7,488,603 B2 | * | 2/2009 | Gjerde | G01N 35/10 210/198.2 |
| 8,377,715 B2 | * | 2/2013 | Suh | B01J 20/3244 422/524 |

FOREIGN PATENT DOCUMENTS

WO  2013/124474  † 8/2013

OTHER PUBLICATIONS

Kumar, Ashok; Srivastava, Akshay; "Cell separation using cryogel-based affinity chromatography" Nature Protocols, 5, 1737-1747, 2010.*
Hertz, CM; et al; "Use of Cell Affinity Chromatography for Separation of Lymphocyte Subpopulations " Biotechnology and Bioengineering, 27, 603-612, 1985.*

\* cited by examiner
† cited by third party

*Primary Examiner* — Renee Claytor
*Assistant Examiner* — David Berke-Schlessel
(74) *Attorney, Agent, or Firm* — Sue S. Kalman

(57) ABSTRACT

This invention relates to devices and methods for purifying biological cells. For example, viable tumor, stem, immune and sperm cells can be purified from a complex biological sample using a column, including a pipette tip column. Cells can be purified in a sealed chromatographic system. Methods of the invention can aid research, diagnosis and treatment of cancer.

22 Claims, 18 Drawing Sheets

Flag Anti-Flag
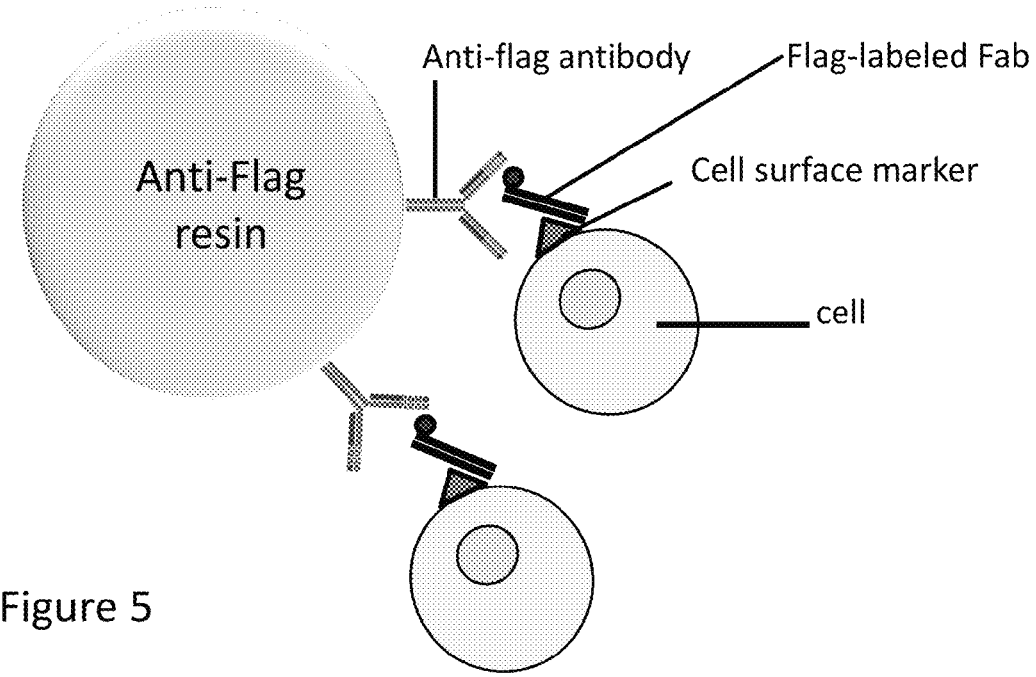
Figure 5
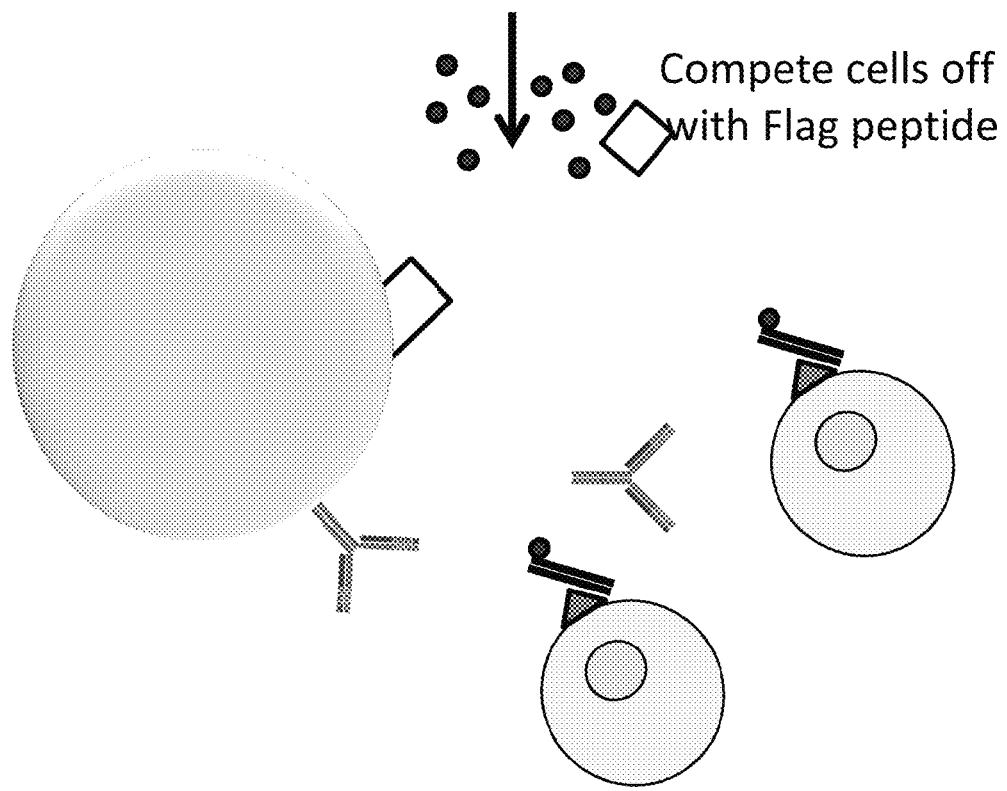

Low pH Elution

A

B

DEVICES AND METHODS FOR PURIFICATION OF BIOLOGICAL CELLS

CROSS REFERENCE TO RELATED APPLICATIONS

This application claims the benefit of U.S. Provisional Application No. 61/913,190, filed Dec. 6, 2013, which is incorporated by reference herein.

FIELD OF THE INVENTION

This invention relates to devices and methods for purifying biological cells. A variety of cell types can be purified from a complex biological sample using a column. The method can be performed quickly and viable cells can be recovered.

SUMMARY OF THE INVENTION

In the present invention, cells are purified from a biological sample using a column. The sample is passed through the column and cells are captured on the solid phase within the column. The solid phase can be a chromatography medium such as a gel resin. Following capture, the column is washed to remove material that is not specifically bound to the column medium. In some embodiments, cells can be recovered by passing an eluent through the column while in other embodiments, cells can be manipulated or interrogated on the column.

BACKGROUND OF THE INVENTION

The primary technology for capturing cells is magnetic beads. In this technology, a suspension of beads is used to treat a sample containing cells. The magnetic beads contain a tag or chemical entity that is selective for cells or for a certain cell type within the sample. After the cells become associated with the magnetic beads, a magnet is used to collect the magnetic beads and captured cells. The magnetic beads may be re-suspended several times with wash solutions to clean the cells. Finally, a solution can be used to release the cells from the beads and a magnet separates the magnetic beads from the cells.

With magnetic beads, cells can be selected either positively or negatively with respect to particular antigens. With positive selection, cells expressing the antigen(s) of interest attach to magnetic beads which in turn attach to the magnetic column as described above. This method is useful for isolation of a particular cell type, for instance CD4 lymphocytes. In negative selection, antibodies are directed against surface antigen(s) present on cells that are not of interest. The undesired cells bind magnetic beads which bind the column and the fraction that goes through is collected, as it contains almost no undesired cells.

However, magnetic beads can negatively impact cell viability. This problem is mitigated somewhat by the use of magnetic nanoparticles. The magnetic-activated cell sorting (MACS) method available from Miltenyl Biotec utilizes magnetic nanoparticles to isolate cells. Cells expressing particular surface antigens attach to the magnetic nanoparticles.

The isolation of circulating tumor cells (CTCs) from blood is an area of very active interest at present. These cells which are shed into the vasculature from a primary tumor circulate in the bloodstream and constitute seeds for subsequent growth of additional tumors (metastasis) in vital distant organs. CTCs present in the bloodstream of patients with cancer provide a potentially accessible source for detection, characterization, and monitoring of non-hematological cancers.

Recently, a number of different technologies have become available for isolation and quantitation of CTCs present in blood. Some technologies exploit the physical properties of CTCs which are generally larger and stiffer than blood cells. CellSieve by Creatv Microtech and ScreenCell CC cartridge by ScreenCell perform size-based separations on blood to isolate CTCs. Although these approaches have potential, CTCs may vary in size and can be vulnerable to shear stress.

Other platforms utilize antibodies against a protein called epithelial cell adhesion molecule (EpCAM) which is found on epithelial cell tumor cells such as those found in breast, prostate and colon cancer. For example, the CellSearch system by Veridex is an FDA-approved method that uses ferrofluids loaded with EpCAM to capture CTCs. Although this system is widely accepted, the sensitivity is low, giving rise to false negatives.

There are also microfluidic devices that capture these EpCAM-expressing cells using antibody-coated micro-posts or channels. In a first generation device, 78,000 antibody-functionalized micro-posts were used to separate cells. Another microfluidic mixing device called the herringbone-chip is made up of parallel slanted channels (Li et al, Lab Chip, 13, 602). These microfluidic devices are continuing to improve.

These magnetic bead methods and chip based columns are slow and do not always produce pure cell populations. In addition, cells isolated on magnetic beads are may not be viable. There exists a need for a column technology that rapidly captures highly concentrations of cells, particularly viable cells at high concentrations and then recovers the cells at high purity.

BRIEF DESCRIPTION OF THE INVENTION

The devices and methods of the invention can be used for the purification of cells, including viable cells and cancer cells. A biological sample containing cells is passed through a column containing a solid phase and cells are captured on the solid phase. In some embodiments, the column is a pipette tip column. Cells can be manipulated or interrogated while bound to the solid phase or cells can be eluted from the column. In some embodiment the flow of sample through the column is bidirectional. In some embodiments the flow rate is quite high so that the cell purification can be performed in 3 hours or less. In certain embodiments, cells can be purified from a sample in less than 30 minutes. The methods of the invention are quite versatile; many cell types can be isolated and a wide variety of applications are possible.

BRIEF DESCRIPTION OF THE DRAWINGS

FIG. 5 is a depiction of an embodiment of a flag competition elution strategy.

SUMMARY OF THE INVENTION

Figure 1:
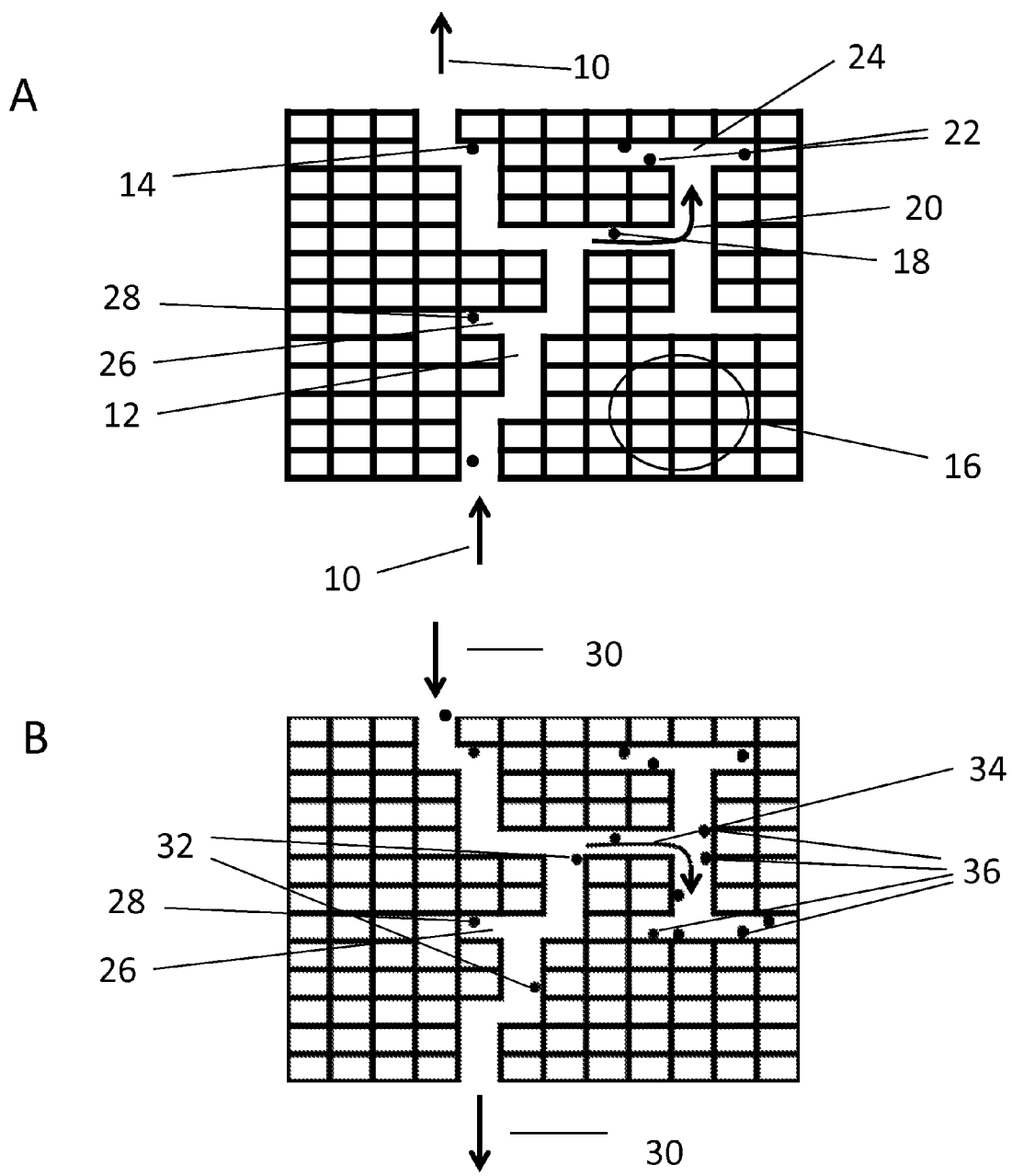
FIG. 1. Stylistic depiction of flow path, nooks and traps in a column. A depicts an aspiration step. B depicts an expulsion step.

In the methods of the invention, whole cells are isolated using a column that contains a bed of medium. In some embodiments, viable cells are isolated from the column. Cells are defined herein as membrane-bound structures that occur as functional units of life (such as in unicellular organisms, e.g. bacteria, protozoa, etc.), or as structural or fundamental units in a biological tissue specialized to perform a particular function in multicellular organisms (e.g. plants and animals). Self-replication is not a necessary property of cells as defined herein; the definition includes entities such as viruses, parasites and exosomes.

Cells are quite fragile and can rupture easily from a variety of physical conditions such as encountering an object, shearing force, turbulence or incorrect solute concentration. Mechanical cell lysis can be induced by a collision of the cells with micro beads. In fact, this is a common method for cell lysis. However, even a little damage, even one breach of the cell membrane is enough to cause catastrophic damage to a cell. Viable cells can die in vitro simply from incorrect storage, processing, transport, exposure to incorrect temperature (heat or cold), pH, medium, vessel, collision with a sharp edge or small passage, etc. Yet, in order to purify cells quickly with a column process, it is important that cells are passed through a column rapidly to be able to capture, wash and recover cells as quickly as possible. This is especially true when the volume from which the cells are being captured is large.

Even though it is important to pass cells through a column quickly, prior art columns have not been able to do this (Braun, R., et al., Journal of Immunological Methods 1982 54, 251-258, Bonnafous et al., J. Immunol. Methods 1983 Mar. 11; 58 (1-2):93-107 and Ohba, H., et al, Cancer Letters (2002) 184, 207-214). In a few cases, cells have been captured on a column using an incubation process where a small sample is applied to the column and then the sample/column is held or incubated in order to capture cells onto the column. Remarkably and in contrast to the prior art, it is possible that the instant method of passing cells through the column rapidly without harm may also help or facilitate the improved capture of the cells from flowing samples and large samples.

It is quite remarkable that intact cells and even viable cells can be captured and purified using the columns and methods of the invention. It is surprising that cells can remain intact even after subjecting them to the methods of the invention. Specifically, cells purified via the instant invention are subjected to a repeated back and forth flow battering motion through a fritted column containing a bed of medium. That is, cells can be passed rapidly through a column containing a bed of medium.

The use of whole cells is a superior format for cell-based assays for a number of reasons. First, it's possible to work with viable cells, which is closer to an in vivo environment than working with for example, a single protein. In whole cells, targets such as cell surface proteins or protein complexes are likely to be intact and in their native state with respect to folding, etc. Interactions between cells can be studied in some embodiments. Cell signaling pathways can be targeted.

In addition, using cells with column processes has a number of advantages. Columns can be operated in parallel and their operation can be automated. Columns can be sterilized and operated in a sterile environment such as a laminar flow hood. Column processes are relatively gentle; there is no shaking, spinning or exposure to magnets. The kinetics of drug-target interactions can be examined in a column as described below. Cells, molecules or compounds can be added to columns serially to examine the results of each addition. Cells can be isolated quickly on the columns of the invention which aids in the retention of viability.

Column processes with cells give an increased signal to noise ratio when compared to other cell-based assays. Due to the large surface area of the beads, cells can be concentrated at the capture step to increase signal. Wash steps remove non-specifically bound material, reducing noise. As a result, They are more sensitive because of reduced noise and yield better statistical data because of the increased signal.

As described above, the columns of the invention contain a bed of medium onto which the cells are captured. The bed can be comprised of beads or particles held in the column by at least one frit below the bed. In certain embodiments, the bed is retained in the column with two frits; one below the bed and one above the bed. It is quite surprising that cells can pass through the frit(s) and the bed of medium and maintain their integrity and in some cases, even their viability.

Consider the physical environment of a liquid sample comprised of cells passing through the frit and bed of medium within a column. The channels through which a cell might flow are not open or linear. Instead, the flow path would consist of a variety of interwoven channels, each with varying and perhaps restrictive diameters, and many possible dead ends marked by repeated turns, bends, winding and twisting. This tortuous path environment is advantageous for the capture of small molecule analytes because the fluid (containing the analyte) gets extensive exposure to the column matrix. However, a cell travelling through this environment could easily be trapped. Adding a frit to the column makes the flow path even more tortuous and restrictive. Of course, physically trapping cells within the column matrix is an undesirable outcome quite distinct from targeted cell capture strategies such as affinity binding. Cells that become physically trapped cannot be recovered with an eluent or desorption solvent. Furthermore, if cells are trapped, even temporarily, they could readily rupture or die. This trapping phenomenon was referred by Bonnafous et al. (supra) and teaches away from successful purification of cells by the instant invention.

The columns of this invention have very low back pressures. The columns are packed and constructed to produce these very low backpressures. The columns of the invention have lower backpressures even compared to columns having low back pressure screen frits similar used in previous column technology in which smaller column bed sizes and column body sizes were used. However, the backpressure of the columns of the invention is significantly lower than these earlier columns. In addition, the columns are packed in such a way that the flow of cells is less restricted and does not harm the cells.

Larger columns usually have higher backpressure than smaller columns. This problem is compounded when the columns are operated with low pressure pumps. Pumps such as syringe pumps or pipette pumps apply positive pressure (head pressure) or vacuum to the column to force the flow of fluid through the column. The pressures applied are low and pumping fluids through large columns is limited. As a result, it is more difficult to pump sample and buffers through large bed column resulting in slower flow rates and longer separation times. This can be problem for capturing and recovering cells. Longer residence times in a column will harm the quality of the cells recovered and could prevent the recovery of cells, particularly viable cells.

FIG. 1 illustrates the surprising nature of the invention. It is a stylistic depiction of the many potential hazards and pitfalls that could be encountered by cells travelling through a column using bidirectional flow. FIG. 1A depicts an aspiration step in which the flow direction 10 is upward. The matrix of the material (e.g., a polymer) is depicted by closed squares 16. Cells cannot penetrate matrix 16. The flow path through a column bed contains many potential nooks and traps for cells. A clear unrestricted flow path 12 enters and exits the bed. Some cells (e.g., 14) may be captured by the column in flow path 12. As the flow proceeds, many or most of the cells 18 enter dead end flow paths 20 to trap the cells 22 in dead end or restricted passages 24. There are also nooks (e.g., 26) just off flow path 12 that may trap cell 28.

FIG. 1B depicts the fate of cells resulting from back and forth flow through the column. The flow direction 30 is in a downward direction, reversed from upward direction 10 shown in FIG. 1A. Although increased residence time may allow a greater number of cells 32 to be captured, especially from a flowing stream, this reversal of the flow direction 34 can also exacerbate the undesired trapping of many cells 36. It should be noted that cell 28 remains trapped in nook 26.

Figure 2:
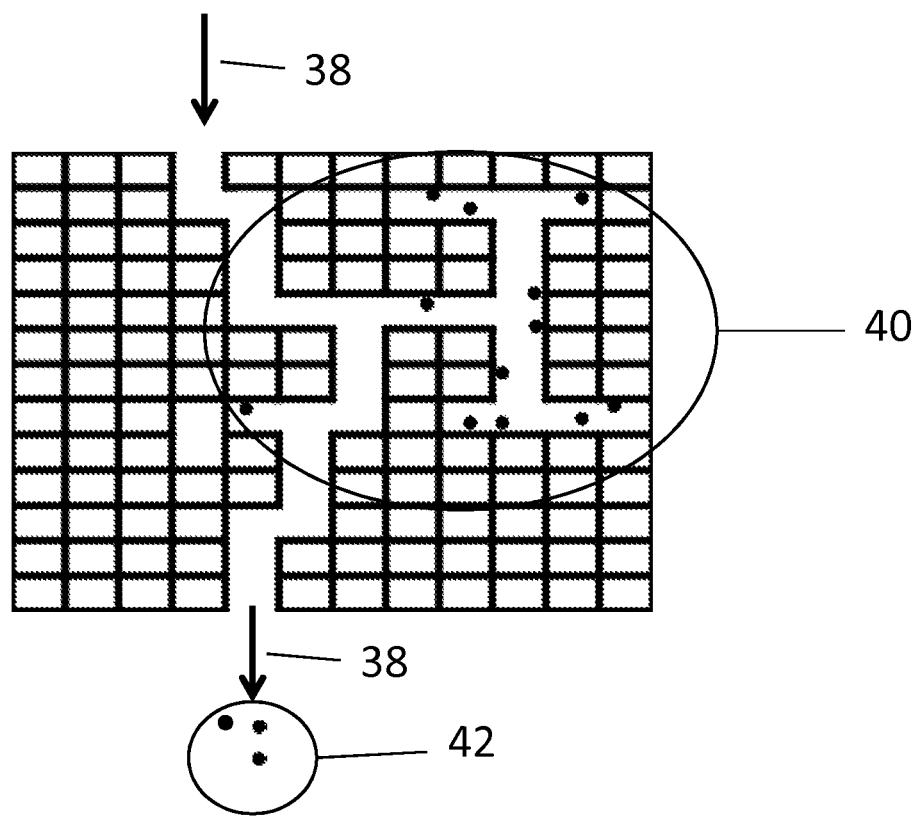
FIG. 2. Elution of cells from a column shown in FIG. 1.

FIG. 2 depicts the elution of cells from a column. The recovery of cells from a column is attempted with a downward flow direction 38. Most of the cells 40 remain irreversibly trapped. A few cells 42 may be recovered but may or may not be intact. In addition to the risk of cell trapping, a person of skill in the art would expect the column environment or materials to be inhospitable to cells. It is desirable to recover intact and even viable cells. Intact cells are defined herein as cells having no holes or ruptures in their membrane. The column materials or surfaces, such as the frit or column walls might be incompatible with the cell integrity or viability. Protrusions present in the column wall, bed or frit could easily damage or rupture cells.

Figure 3:
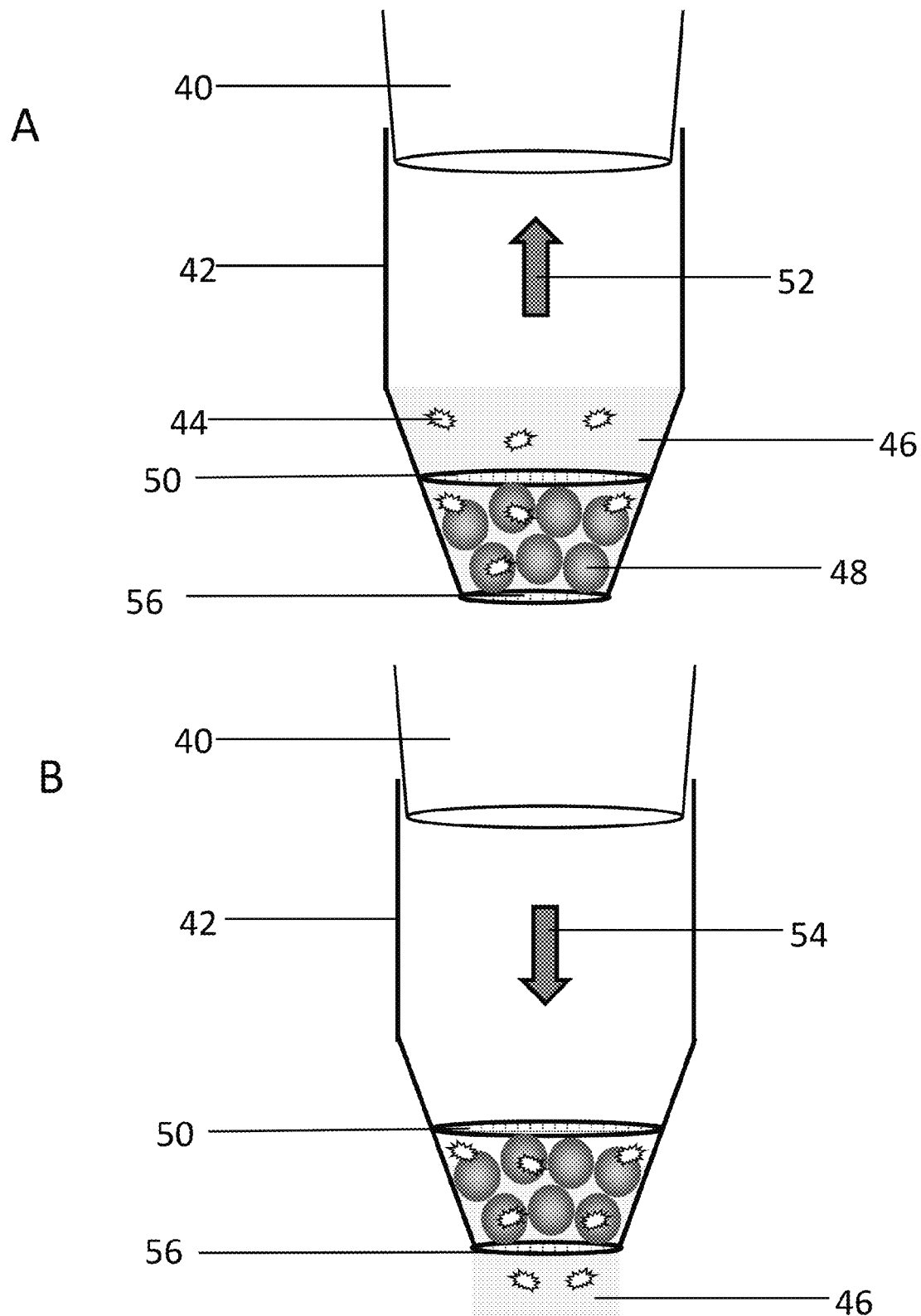
FIG. 3. Depiction of the column and method of the invention. A depicts and aspiration step and B depicts and expulsion.

FIG. 3 depicts a column and method of the invention. Cells in a liquid sample are passed through the column using back and forth flow. In these embodiments, the upper end of the column is operatively engaged with pump 40 and sample 46 containing cells 44 is aspirated and expelled through the lower end of the column. During the aspiration step, the sample travels in direction 52, upwards in through lower frit 56 into the bed of beads 48 and then continues through upper frit 50 (FIG. 3A). During expulsion, the sample 46 travels back downward in direction 54, back through upper frit 50, into the bed of medium, through lower frit 56 and exits the bottom of the column (FIG. 3B). These aspirations and expulsions can be repeated multiple times, the desired result being that intact cells are captured by the medium.

Intuitively, it seems that the flow paths resulting from back and forth flow would be even more perilous for cells than unidirectional flow, especially when the goal is recovery of viable cells or even intact cells. Cells would pass through the column bed and frit(s) multiple times from both directions, increasing the probability of cell damage or death.

DETAILED DESCRIPTION OF THE INVENTION

This invention provides devices and methods for isolation of cells using a column format. The cells can be eukaryotic or prokaryotic. The term cells, as used herein is not limited to self-replicating entities. Included in the definition are viruses, exosomes and parasites.

In certain embodiments, the isolated cells are viable. In some applications, the maintenance of cell viability is less important. For example, cells purified on the column may be counted, labeled, analyzed by DNA sequencing, PCR or other assays.

The Sample

The starting sample is usually a heterogeneous mixture from which cells are purified. The sample can be from any biological source and can contain viable cells. For example, cells can be captured from biological fluids such as blood, urine, saliva, spinal fluid or semen, tissues such as brain or tumor tissue and other samples such as fecal (stool) or hair. In certain embodiments, sample preparation steps are performed prior to the isolation of cells on a column. For example, when cells are captured from blood, the blood can be fractionated by centrifugation and only the buffy coat loaded on the column. Alternatively, whole blood can be diluted or loaded directly on the column.

Cells isolated using methods and devices of the invention are not limited to a particular cell type; cells captured by the methods of the invention can be eukaryotic or prokaryotic cells. Eukaryotic cells can be from protozoa, chromists, plants, fungi or animals such as mammals, amphibians, birds, fish, reptiles and invertebrates.

In certain embodiments, the devices and methods can be used for the analysis of cells from crime scene samples. A non-limiting list of cells that can be isolated by the columns of the invention includes epithelial cells, hormone secreting cells, sensory transducer cells, neuron cells, glial cells, lens cells, metabolic cells, storage cells, barrier function cells such as lung, gut, exocrine glands and urogenital tract, kidney cells, extracellular matrix cells, contractile cells, blood and immune system cells, germ cells, nurse cells, interstitial cells, activated B-cells, mature B-cells, cytotoxic T-cells, helper T-cells, activated T-cells, natural killer (NK) cell, monocyte and macrophage, activated macrophage, endothelial cell, smooth muscle cell, dendritic cell, mast cell, fibroblast (stromal), epithelial cell, adipocyte, stem cells, granulocytes, platelets, erythrocytes circulating tumor cells, Alexander cells, astroglia, B Lymphoblast, B Lymphocyte, basophil, cortical neurons, cutaneous T cells, lymphocytes, embryonic cells, enterocytes, epithelial cells, transformed cells, immortalized cells, large T antigen, epithelial neuroendocrine, erythroblast, fetal, fibroblast, glial cell, glioblastoma, Hela cells, histocyte, human papillomavirus, hybridoma: e.g., helper T lymphocyte, keratinocyte, killer cell, large cell, lymphoblast, lymphoblast B lymphocyte, lymphoblast Human Immunodeficiency Virus, Lymphocyte, medulloblastoma, megakaryoblast, melanocyte, melanoma, monoblast, myeloblast, neuroblast, neuroendocrine, osteoblast, pluripotent stem cell, pre-B lymphoblast, promyeloblast, retinoblastoma, Schwann cell, squamous cell, T lymphoblast, T lymphocyte, T-cell.

Cells isolated can be from any tissue. A non-limiting list of tissue type examples follows. lung, ascites, bone marrow, bone, brain, cervix, colon, connective tissue, duodenum, eye, Kidney: Skin, Kidney, Liver, Lung, Lung: Pleural Effusion, Mammary Gland, Ovary: Ascites, Ovary, Pancreas: Lymph Node, Pancreas, Peripheral Blood, Pharynx, Placenta, Prostate, Retinal Pigmented Epithelium, Skin, Spleen, Stomach: Derived From Metastatic Pleural Effusion, Stomach, Submaxillary Salivary Gland, Testes, Thyroid, Tongue, Urinary Bladder, Uterus, Adrenal Gland, Airway Epithelium, Aorta, Bladder, Blood, Bone Marrow, Brain, Breast, Breast Derived From Metastatic Site: Pleural Fluid, Bronchiole, Bronchus, Carcinoma, Cecum, Cord Blood, Cornea, Ectocervix, Embryo, Embryonic Kidney, Endocervix, Endometrium, Epithelium, Esophagus, Eye, Fetus, Foreskin, Gingival Biopsy, Heteromyeloma, Intestine, Kidney, Lung Adenocarcinoma, Lymph Node, Lymph Node Derived From metastatic Site: Peritoneal effusion, mammary gland, marrow, mesencephalon, mesothelium, muscle, nasal Septum, nervous, palatal, palatal mesenchyme, pancreas, peripheral Blood, peritoneal Effusion, peritoneum, peritonial Effusion, pharynx: Derived From Metastatic Site: pleural Effusion, pleura, pleural Effusion, prostate, Rectum, Retina, Retroperitoneal Embryonal Tumor, Retroperitoneum, skin: derived From Metastatic Axillary Node, Skin: Derived From Metastasis On Skin Of Thigh, Small Intestine, Somatic cell Hybrid, Stomach, Submaxillary, Synovium, testis, thymus, thyroid, tonsil, trachea, trunk, umbilical vein, ureter, uterine, vagina, vascular, vein, vertebral epitheloid carcinoma and vulva.

The Columns

Columns used in the invention contain material capable of capturing cells. In certain embodiments, the columns are comprised of a packed bed of medium. In other embodiments, the columns can contain a fluidized bed or a bed that packed in such a way that the beads are not compressed and the flow path will not be restricted. Using this method, the resin can pack and form channels in such a way that cells can move through the resin with reduced chance of damage and an increased chance of capture.

The column packing of the invention can be described functionally. Columns that are packed properly allow cells to pass through the bed without being trapped within the resin. In a column packed for use with cells and lacking an affinity group for capture, at least 90% of the cells can pass through the column bed without being trapped. In some embodiments, at least 90%, at least 95%, at least 96%, at least 97%, at least 98% or at least 99% of the cells can pass through the column without being trapped. Cells can pass through the columns without being trapped using unidirectional or bidirectional flow.

The columns of the invention are comprised of a medium on which the cells are captured. The medium can be beads or particles. In certain embodiments, the column medium can be a monolith, a filter or a combination of materials. In some embodiments, the bead size is quite large, on the order of 100-900 microns or in some cases even up to a diameter of 3 mm. In other embodiments, the bead size is that used in conventional columns, on the order of 45-150 microns. The average particle diameters of beads of the invention can be in the range of about 20 µm to several millimeters, e.g., diameters in ranges having lower limits of 20 µm, 30 µm, 40 µm, 50 µm, 60 µm, 70 µm, 80 µm, 90 µm, 100 µm, 150 µm, 200 µm, 300 µm, or 500 µm, and upper limits of 20 µm, 30 µm, 40 µm, 50 µm, 60 µm, 70 µm, 80 µm, 90 µm, 100 µm, 150 µm, 200 µm, 300 µm, 500 µm, 750 µm, 1 mm, 2 mm, or 3 mm.

In some embodiments, the columns used for the methods of the invention are pipette tip columns. Pipette tip columns are defined herein as columns capable of operative engagement with a pipette, syringe or liquid handing robot, or any pumping device that can impart positive and negative pressures to liquids to force the liquid through the column in a back and forth manner. In certain embodiments, the columns can be integrated into a multi-well plate. In other embodiments, the column is a syringe.

In certain embodiments of the invention, one or more frits are used to contain the bed of medium within a column. Frits can take a variety of forms, and can be constructed from a variety of materials, e.g., polymer, glass, ceramic, metal, fiber. The frits of the invention are porous, since it is necessary for fluid to be able to pass through the frit. The frit should have sufficient structural strength and integrity to contain the medium in the column. It is desirable that the frit have little or no affinity for liquids or cells with which it will come into contact during the column use. Thus, in many embodiments of the invention, it desirable to use a frit that has a minimal tendency to bind or otherwise interact with cells.

Frits of various pores sizes and pore densities may be used provided the free flow of liquid is possible and the solid phase is held in place. Frits of pore size large enough to prevent plugging with cells or cell debris are of particular interest.

In certain embodiments, one frit (e.g., a lower, or bottom, frit) is bonded to and extends across the open channel of the column body. Preferably, the bottom frit is attached at or near the open lower end of the column, e.g., bonded to and extend across the open lower end. Normally, a bed of separation media, is positioned inside the open channel and in contact with the bottom frit.

In certain embodiments, a top frit may be employed. For example, in some embodiments, a second frit is bonded to and extends across the open channel between the bottom frit and the open upper end of the column body. In this embodiment, the top frit, bottom frit and column body (i.e., the inner surface of the channel) define a media chamber wherein a bed of medium is positioned. The frits should be securely attached to the column body and extend across the opening and/or open end so as to completely occlude the channel, thereby substantially confining the bed of medium inside the media chamber. In some embodiments of the invention, the bed of medium occupies at least 50% of the volume of the media chamber, more preferably 80%, 90%, 95%, or substantially 100% of the volume. In certain embodiments, the invention, the space between the bed of medium and the upper and lower frits is negligible, i.e., the frits are in substantial contact with upper and lower surfaces of the media bed, holding a well-packed bed of medium securely in place.

In some embodiments of the invention, the bottom frit is located at the open lower end of the column body. This configuration is not required, i.e., in some embodiments, the bottom frit is located at some distance up the column body from the open lower end. However, in view of the advantage the come with minimizing dead volume in the column, it is desirable that the lower frit and media chamber be located at or near the lower end. In some cases, this can mean that the bottom frit is attached to the face of the open lower end. However, in some cases there can be some portion of the lower end extending beyond the bottom frit. For the purposes of this invention, so long as the length of this extension is such that it does not substantially introduce dead volume into the column or otherwise adversely impact the function of the column, the bottom frit is considered to be located at the lower end of the column body. In some embodiments of the invention, the volume defined by the bottom frit, channel surface, and the face of the open lower end (i.e., the channel volume below the bottom frit) is less than the volume of the media chamber, or less than 10% of the volume of the media chamber, or less than 1% of the volume of the media chamber.

In some embodiments of the invention, the media chamber is positioned near one end of the column, which for purposes of explanation will be described as the bottom end of the column. The area of the column body channel above the media chamber can be quite large in relation to the size of the media chamber. For example, in some embodiments the volume of the media chamber is equal to less than 50%, less than 20%, less than 10%, less than 5%, less than 2%, less than 1% or less than 0.5% of the total internal volume of the column body. In operation, solvent can flow through the open lower end of the column, through the bed of medium and out of the media chamber into the section of the channel above the chamber. For example, when the column body is a pipette tip, the open upper end of the pipette tip can be fitted to a pipette and a solution drawn through the medium into the upper part of the channel.

Some embodiments of the invention employ large pore size frit. Frits of the invention preferably have pore openings or mesh openings of a size in the range of about 5-500 μm. In certain embodiments, the pore size is 10-200 μm, 33-150 μm, e.g., about 33-43 μm. The performance of the column is typically enhanced by the use of frits having pore or mesh openings sufficiently large so as to minimize the plugging from cells and biological particulates. For columns of larger diameter, frit pore size of 20, 33, 37 and 43 μm pore size are acceptable. Increasing the frit pore size can only be done if the particle size of the packing can be increased.

The space between the resin particles is important also. The space can increase with a looser packing of the column. This space may provide flow channels suitable for capture, washing and recovery of cells without trapping the cells within the packing material.

The use of membrane screens typically provides this low resistance to flow and hence better flow rates, reduced back pressure and minimal distortion of the bed of media. The pore or mesh openings of course should not be so large that they are unable to adequately contain the medium in the chamber.

Some embodiments of the invention employ a relatively thin frit, preferably less than 2000 μm in thickness (e.g., in the range of 20-2000 μm, 40-350 μm, or 50-350 μm). In certain embodiments, the frits are less than 200 μm thick (e.g., in the range of 20-200 μm, 40-200 μm, or 50-200 μm), or less than 100 μm in thickness (e.g., in the range of 20-100 μm, 40-100 μm, or 50-100 μm). However, thicker frits can also be used in some embodiments, up to several mm, 5 and even 10 mm, thick may be used if the pore size of the frit can be increased dramatically.

Certain embodiments of the invention employ a membrane screen as the frit. The membrane screen should be strong enough to not only contain the medium in the column bed, but also to avoid becoming detached or punctured during the actual packing of the media into the column bed. Membranes can be fragile, and in some embodiments must be contained in a framework to maintain their integrity during use. However, it is desirable to use a membrane of sufficient strength such that it can be used without reliance on such a framework.

The membrane can be a woven or non-woven mesh of fibers that may be a mesh weave, a random orientated mat of fibers i.e. a "polymer paper", a spun bonded mesh, an etched or "pore drilled" paper or membrane such as nuclear track etched membrane or an electrolytic mesh (see, e.g., U.S. Pat. No. 5,556,598). The membrane may be, e.g., polymer, glass, or metal provided the membrane is low dead volume, allows movement of the various cell samples and processing liquids through the column bed, may be attached to the column body, is strong enough to withstand the bed packing process, is strong enough to hold the column bed of beads, and does not interfere with the column process i.e. does not adsorb or denature the sample.

The frit can be attached to the column body by any means which results in a stable attachment. For example, the screen can be bonded to the column body through welding or gluing. Gluing can be done with any suitable glue, e.g., silicone, cyanoacrylate glue, epoxy glue, and the like. The glue or weld joint must have the strength required to withstand the process of packing the bed of medium and to contain the medium with the chamber. For glue joints, a glue should be employed that does not adsorb or denature cells.

For example, glue can be used to attach a membrane to the tip of a pipette tip-based column, i.e., a column wherein the column body is a pipette tip. A suitable glue is applied to the end of the tip. In some cases, a rod may be inserted into the tip to prevent the glue from spreading beyond the face of the body. After the glue is applied, the tip is brought into contact with the membrane frit, thereby attaching the membrane to the tip. After attachment, the tip and membrane may be brought down against a hard flat surface and rubbed in a circular motion to ensure complete attachment of the membrane to the column body. After drying, the excess membrane may be trimmed from the column with a razor blade.

Alternatively, the column body can be welded to the membrane by melting the body into the membrane, or melting the membrane into the body, or both. In one method, a membrane is chosen such that its melting temperature is higher than the melting temperature of the body. The membrane is placed on a surface, and the body is brought down to the membrane and heated, whereby the face of the body will melt and weld the membrane to the body. The body may be heated by any of a variety of means, e.g., with a hot flat surface, hot air or ultrasonically. Immediately after welding, the weld may be cooled with air or other gas to improve the likelihood that the weld does not break apart.

Alternatively, a frit can be attached by means of an annular pip, as described in U.S. Pat. No. 5,833,927. This mode of attachment is particularly suited to embodiment where the frit is a membrane screen.

The frits of the invention, e.g., a membrane screens, can be made from any material that has the required physical properties as described herein. Examples of suitable materials include nylon, polyester, polyamide, polycarbonate, cellulose, polyethylene, nitrocellulose, cellulose acetate, polyvinylidine difluoride, polytetrafluoroethylene (PTFE), polypropylene, polysulfone, PEEK, PVC, metal and glass. A specific example of a membrane screen is the 43 µm pore size Spectra/Mesh® polyester mesh material which is available from Spectrum Labs (Ranch Dominguez, Calif., PN 145837).

Pore size characteristics of membrane filters can be determined, for example, by use of method #F316-30, published by ASTM International, entitled "Standard Test Methods for Pore Size Characteristics of Membrane Filters by Bubble Point and Mean Flow Pore Test". The columns of the invention can be made in a wide range of sizes. Column bodies can range from a 10 µl pipette tip to a 100-ml column. These large volume columns are described in more detail below. Of course, larger columns can be used to process larger liquid volumes. For example, a 20-ml pipette tip column containing 1 ml of resin can accommodate approximately 19 ml of a biological liquid sample.

Sterile Columns

In certain embodiments, the columns are sterile. In these embodiments, the columns can be assembled from sterile components in a sterile setting such as a clean room. Components can be sterilized by methods known in the art such as filtration, irradiation, chemicals and heat.

Alternatively, terminal sterilization can be performed. Terminal sterilization is defined herein as sterilization of the manufactured columns. In this embodiment, the columns can be assembled, packaged and then sterilized prior to use. Terminal sterilization is desirable because the change of contamination during assembly is eliminated.

Column sterilization after manufacture can be performed by a number of methodologies. In one embodiment, columns can be assembled and then sterilized by autoclaving as described in the examples below. Alternatively, terminal sterilization can be performed by irradiation.

In certain embodiments, the column medium is a hydrated gel resin. In these embodiments, the resin may be coated with a high boiling point liquid prior to use as described in U.S. Patent Application US20050045543.

Various mechanisms can be used for cell capture on the medium. Non-limiting examples include a functional group that has affinity for the cells, use of a tagged antibody, ion exchange, a tagged aptamer and an antibody loaded resin (Pro A, G etc.) covalent bonded linkers (alkyl thio, etc.), hydrogen bonded linkers. In some embodiments, a biotinylated antibody binds a cell surface marker and cells are isolated using a streptavidin resin. In certain embodiments, the resin can be comprised of an antibody. Other capture mechanisms such as hydrophobic interaction, reverse phase, normal phase, ion pairing and ion exchange can be used as long as the cells are not damaged.

Antibodies used with the invention can bind cell surface markers. There are many commercially-available antibodies that bind cells. One list of over 2800 antibodies can be found using the product finder on the Miltenyl Biotec website.

The following is a non-limiting list of human cell surface markers that can be identified by PCR (See the SABiocsiences website. Lists are also available for mouse and rat cell surface markers.

Activated B-cells: CD28, CD38, CD69, CD80, CD83, CD86, DPP4, FCER2, IL2RA, TNFRSF8, CD70 (TNFSF7).

Mature B-cells: CD19, CD22, CD24, CD37, CD40, CD72, CD74, CD79A, CD79B, CR2, IL1R2, ITGA2, ITGA3, MS4A1, ST6GAL1.

Other B-cell Surface Markers: CD1C, CHST10, HLA-A, HLA-DRA, NT5E.

T-cell surface markers:

Cytotoxic T-cells: CD8A, CD8B.

Helper T-cells: CD4.

Activated T-cells: ALCAM, CD2, CD38, CD40LG, CD69, CD83, CD96, CTLA4, DPP4, HLA-DRA, IL12RB1, IL2RA, ITGA1, TNFRSF4, TNFRSF8, CD70 (TNFSF7).

Other T-cell Surface Markers: CD160, CD28, CD37, CD3D, CD3G, CD247, CD5, CD6, CD7, FAS, KLRB1, KLRD1, NT5E, ST6GAL1.

Natural Killer (NK) cell Surface Markers: CD2, CD244, CD247, CD7, CD96, CHST10, IL12RB1, KLRB1, KLRC1, KLRD1, NCAM1.

Monocyte and Macrophage cell Surface Markers:

Activated Macrophages: CD69, ENG, FCER2, IL2RA.

Other Monocyte and Macrophage Surface Markers: C5AR1, CD163, CD40, CD63, CD74, CD86, CHST10, CSF1R, DPP4, FCGR1A, HLA-DRA, ICAM2, IL1R2, ITGA1, ITGA2, S100A8, TNFRSF8, CD70 (TNFSF7).

Endothelial cell Surface Markers: ENG, ICAM2, NOS3, PECAM1, SELP, TEK, VCAM1, VWF.

Smooth Muscle cell Surface Markers: MYH10, MYH9, MYOCD.

Dendritic cell Surface Markers: CD1A, CD209, CD40, CD83, CD86, CR2, FCER2.

Mast cell Surface Markers: C5AR1, FCER1A, FCER2, TPSAB1.

Fibroblast (Stromal) Surface Markers: ALCAM, COL1A1, COL1A2.

Epithelial cell Surface Markers: CD1D, KRT18, KRT5, KRT8, EPCAM.

Adipocyte Surface Markers: RETN.

The medium may be held in the column with at least one frit positioned below the bed of medium. This lower frit may lie at the lower end of the column or it may be positioned some distance above the lower end. In certain embodiments, a second frit is positioned above the bed.

The bed can be packed between two frits using a light force packing method in which pressure is not used to compact the bed. In alternative embodiments, the column lacks a top frit. In still other embodiments, there is a gap between the bed of medium and the top frit. This gap is referred to as an air gap.

The column frits can additionally be described functionally. The frits have a pore size small enough to contain the medium but large enough for cells to pass through. Frits of the invention preferably have pore openings or mesh openings of a size in the range of about 5-500 µm. In preferred embodiments, the frits can be quite thin. In fact, the frit thickness can be less than 350 microns. The frit or frits should be sufficiently thin such that cells will not become trapped or die within the frit during column operation. It is important that the frit does not provide dead-end or restricted-end flow paths that could potentially trap or damage cells. In some embodiments, a screen or fabric frit is utilized. However, any suitable material that meets the above functional requirements can be used for the frit.

The frits must have specific porosity characteristics. It is not only a matter of having sufficiently large pores. The pore shape is important as well. Pores cannot be destructive or restrictive to cells.

Column Operation

In the methods of the invention, a sample containing cells is passed through a bed of medium or solid phase within a column. The cells are captured on the column medium while other sample constituents pass through the column. The column with captured cells is washed and the purified cells can be released from the column or manipulated on the column.

Although it is not required, columns of the invention may be operated using back and forth flow. In some embodiments, liquids are aspirated and expelled through the lower end of the column. This method is referred to as back and forth or bidirectional flow. In these embodiments, a pump, such as a liquid handling robot is operatively engaged with the upper end of the column and liquids (such as the sample, wash and eluent) are aspirated and expelled through the lower end of the column. Multiple aspirate expel steps are often used with back and forth flow.

In other embodiments, unidirectional flow is used to pass liquids through the column. In these embodiments, fluids are added to the upper end of the column and flows in a downward direction through the column and out the lower end.

The sample can be passed through the column with the use of a pump, a vacuum or even gravity. When unidirectional flow is used, liquids can be passed through the column multiple times. That is, the flow-through can be collected and loaded onto the column again.

The method can be performed in an automated or semi-automated fashion. In some embodiments, the method can be performed manually using a hand-held pipette or a syringe. The term "semi-automated" is defined as a process by which two or more samples, columns or tubes are processed simultaneously. The term "automated" is defined as a process by which sample processing is performed by a robotic system controlled by a timed computer program. This automation process may be performed with columns in parallel. Even though backpressures are low and the capture, wash and purification of cells is a difficult process, columns of the invention may be operated in parallel with automation.

Depending on the sample, it may be desirable to process a large volume of a liquid, e.g., a biological fluid. Sample volumes larger than the column bed or larger than the column body can be processed by repeated aspiration and expulsion of the sample. Alternatively, large sample volumes can be loaded onto the columns through the open upper end and collected from the open lower end. This process can be performed repeatedly in certain embodiments. In some embodiments, the sample is comprised of a flowing stream. In these embodiments, the cells are captured by the column from a stream that is pumped into the column and flows through the column. Because the capture process is from a flowing stream, samples larger than the bed volume of the column can be captured.

Intuitively, it seems that a slow flow rate would be advantageous for the capture of cells on a column. There are several reasons for this. First, the cell surface protein must have the correct orientation to be captured by the antibody (or other capturing group) on an affinity resin. Second, there must be sufficient time for the affinity group to bind and capture the cells. These two parameters improve as the flow rate is decreased. Furthermore, a slow flow rate would be gentler on the cells; they wouldn't be damaged by the solid surface of the media.

However, even when slow flow rates are used, cells travel through the column at relatively high linear velocities. A high linear velocity would be expected to exacerbate the potential problems listed above. For example, a cell could become lodged in a dead end with greater force, making it more difficult to free the cell. While a cell travelling at a relatively slow velocity might slide or sidle around an obstacle, a cell travelling at a high velocity might be ruptured.

However, in the columns of the invention, rapid flow rates are possible. The use of rapid flow rates decreases separation time which positively impacts cell viability. Although the cells may be subjected to more frequent and harder collisions within the column body, they are able to survive even with repeated passes through the column and even with the use of back and forth flow. Even through rapid flow rates would be expected to decrease the opportunity for the cell capture, they allow capture of the cells without damage.

Columns of the invention can accommodate a variety of flow rates, and the invention provides methods employing a wide range of flow rates, oftentimes varying at different steps of the method. In various embodiments, the flow rate of liquid passing through the media bed falls within a range having a lower limit of 0.1 mL/min, 0.5 mL/min, 1 mL/min, 2 mL/min, or 4 mL/min and upper limit of 0.1 mL/min, 0.5 mL/min, 1 mL/min, 2 mL/min, 4 mL/min, 6 mL/min, 10 mL/min, 20 mL/min, 30 mL/min, 40 mL/min, 50 mL/min or greater.

A faster flow rate reduces the time for purification which is advantageous for cell viability. On the other hand, a fast flow rate is more likely to damage the cells.

Columns of the invention are capable of capturing cells from large sample volumes, i.e. samples larger than one bed volume or one column volume. In some embodiments, the sample is comprised of a flowing stream. Prior art columns and methods described by Braun et al., Bonnafous et al. and Ohba et al. (supra) require small volume samples limited to one bed volume and smaller. In addition, these prior art methods teach that it is necessary to incubate the sample for several minutes before the separation process can begin. It appears that these prior art columns required incubation time for the cells to become captured by the resin and therefore were not capable of capturing cells from a flowing sample. Without being bound by theory, it appears the cells had to diffuse or undergo orientation to the affinity site in order for the capture process to occur.

Columns of the invention have flow paths that allow the cells to be captured from flowing streams. Capture is a fast process and so can be performed with a flowing sample. This is a great improvement over the prior art because capture from a flowing stream allows the capture of samples from volumes that are larger than the bed volume and in some cases, larger than the column volume. In one embodiment, the flowing sample stream is aspirated and expelled back and forth through the column at least once In many embodiments, the sample is passed back and forth through the column bed multiple times. There is no practical limit to the number of back and forth cycles although lengthy procedures may be harmful to the cells, particularly viable cells. Also cells traversing the column several times before being captured have a greater chance of becoming damaged or trapped. Capture may be from multiple sample aliquots processed in series or from multiple cycling from a large volume sample aliquot. Capture from a flow stream may be performed with unidirectional flow. In some embodiments, the capture is performed using slow flow rates, 100-200 μL/min but the capture process is still successful with faster flow rates, up to 10 to 40 bed volumes/minute.

When a sample containing cells is passed through the column, at least a portion of the cells are captured by the material within the column. The sample may comprise a variety of cell types, e.g., blood and it may be desirable to capture only one cell type. In some cases, rare cells such as circulating tumor cells are captured on the column medium. In these cases, the cells captured can be a very small percentage of the total number of cells in the sample. In some embodiments, the number of cells captured can be relatively small.

A variety of affinity strategies can be used to capture cells on the column. However, it is also possible to use ion exchange. In alternate embodiments, cell capture may not be desired. Gel filtration (size-exclusion chromatography) can be used to enrich a particular cell type by separating cells away from non-cell components or by separating cells from each other based on their size. For example, circulating tumor cells (CTCs) are larger than other cell types and can be separated from other cells using size exclusion chromatography. Gel filtration could also be used to clean up a sample, e.g. a diagnostic sample. Non-cell material could be removed or taken up by the column.

In some embodiments, the column is operated in a cold room while in other embodiments, the column can be operated at room temperature or at a temperature greater than room temperature. The optimum temperature for running the column will depend on parameters such as the application, the column medium and the cell type. In some embodiments, the columns are operated in a hood such as a laminar flow hood to maintain sterility.

In some embodiments, viable cells can be recovered from the column. In these embodiments, the appropriate liquids for maintenance of cell viability can be used in the columns. However, viable cells are not required for all applications. For example, it may be desirable to determine whether a particular cell type is present in a sample or to perform PCR on cells isolated using the columns and methods of the invention.

After the capture step, the columns can be washed with buffer or water to remove any material that is not specifically bound to the column medium. The wash liquid can be passed through the column by any means or rate described above for the sample. The volume of the wash liquid can be greater than that of the column. The wash step may be repeated once to several times.

Following the column wash, the cells can be eluted from the column by passing an eluent through the column. A variety of elution strategies can be used however, when viable cells are desired, the eluent and elution conditions must be chosen carefully so it will not harm the cells.

Figure 4:
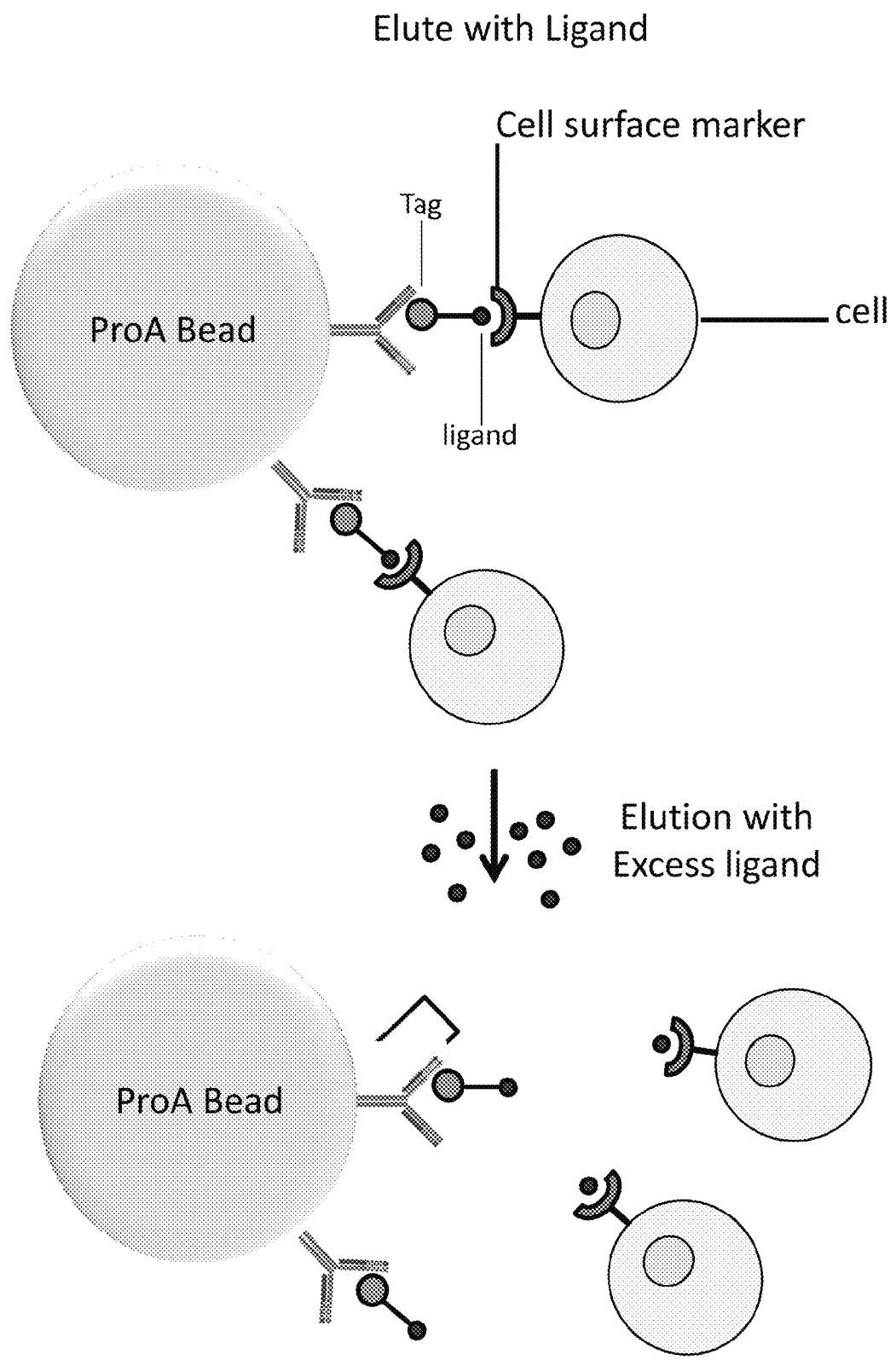
FIG. 4 is a depiction of an embodiment of a ligand competition elution strategy.

Another competition strategy would be to capture cells with a ligand that binds a cell surface marker and then elute the cells with the same ligand. In another example, cells bound to antibodies captured on proA resin can be eluted with proA or a similar molecule. Alternatively, the ligand could be bound to a tag which in turn, binds an antibody as shown in FIG. 4.

A third competition strategy utilizes ANT-FLAG resin. A FLAG-labeled Fab or Antibody that binds a cell surface marker could be engineered e.g., in *E. coli* as shown in FIG. 5.

Figure 6:
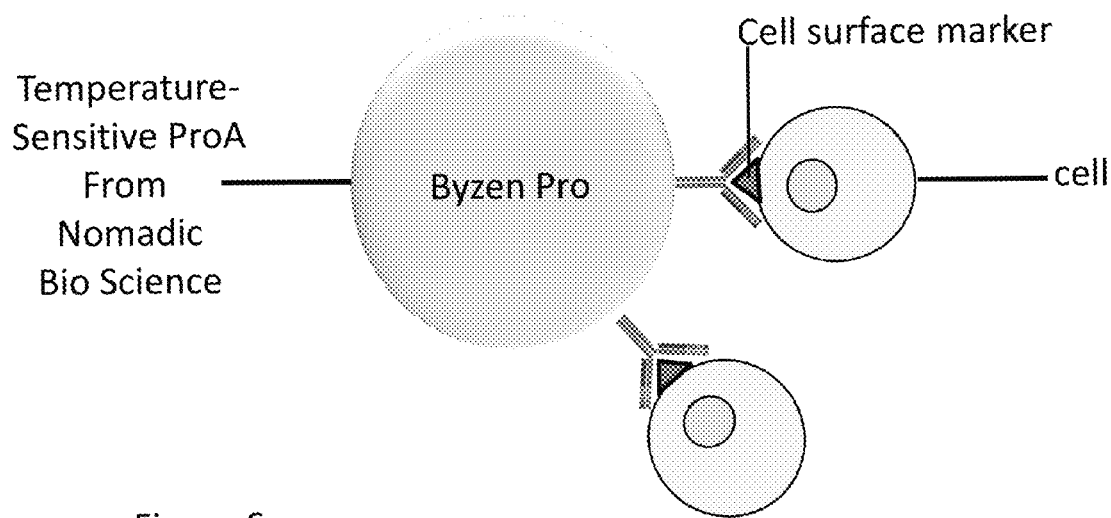
FIG. 6 is a depiction of an embodiment of a temperature-sensitive cell purification.
Figure 6:
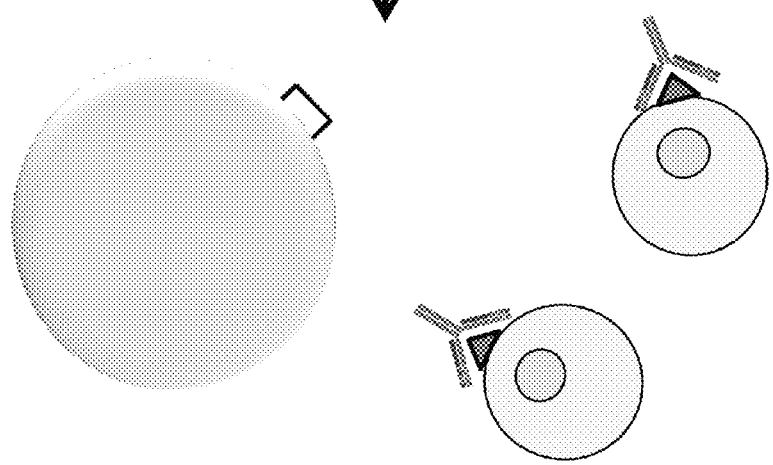
Figure 7:
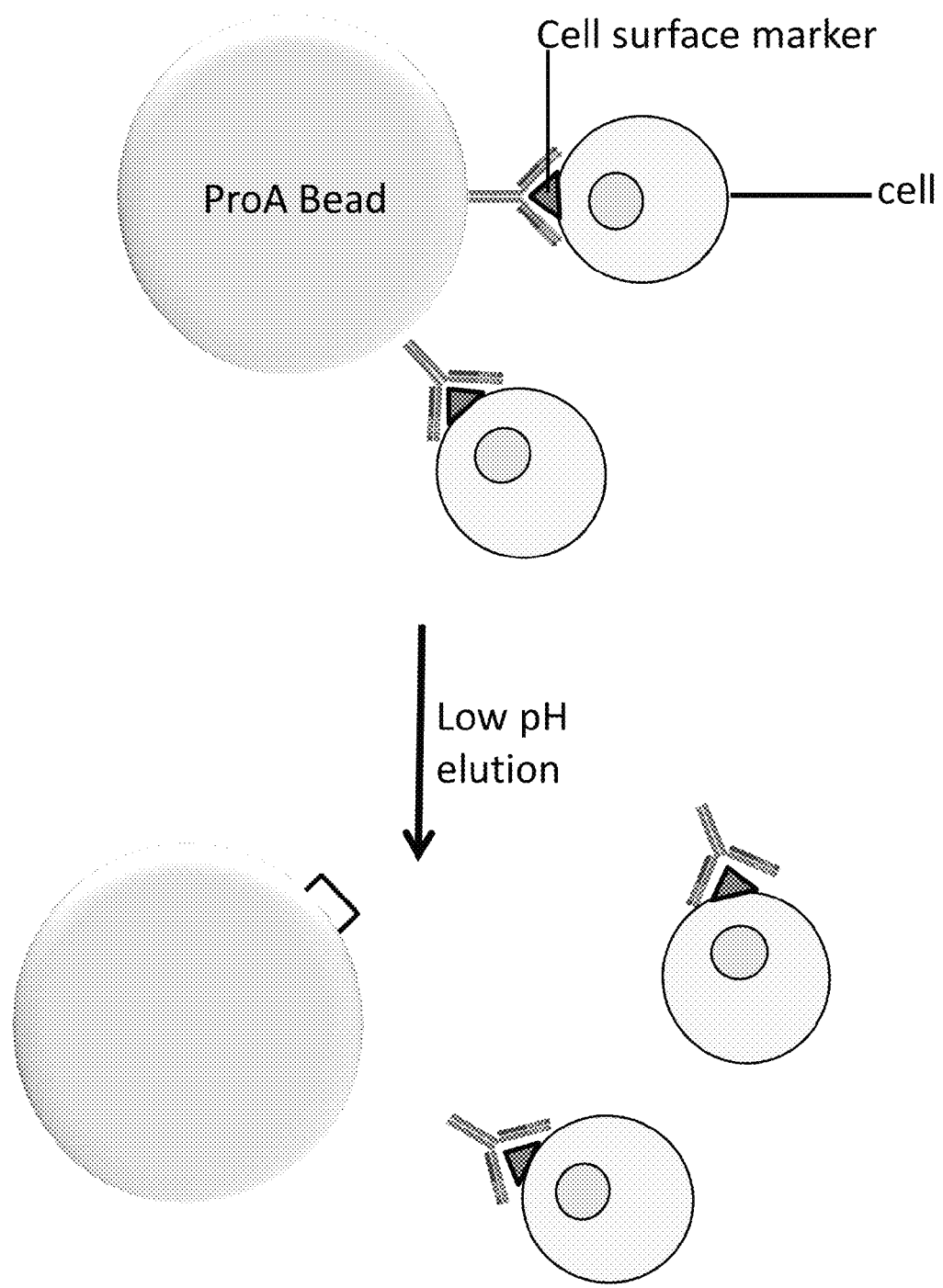
FIG. 7 is a depiction of an embodiment of a low pH elution strategy.

Alternatively, cells can be eluted by a physical change such as a change in pH or temperature. Preferably, an eluent can be selected that does not harm the cells, particularly when the recovery of viable cells is desired. In one example, a temperature-sensitive proA resin can be used such as Byzen Pro resin made by Nomadic Bio Science. Using this type of resin, cells can be eluted at neutral pH by increasing the temperature as shown in FIG. 6. In a second example, cells can be captured by antibodies specific to cell surface markers and eluted using a low-pH eluent (see FIG. 7). In this example, the elution step could be performed rapidly followed by a quick transfer of the purified cells to a neutral-pH solution.

In some embodiments, cells captured on a column can be eluted using enzymatic cleavage. For example, cells could be captured using proA resin charged with antibodies that bind a cell surface marker. The antibody could then be cleaved with an enzyme such as papain or pepsin to elute the cells.

The columns and methods of the invention can be used to capture and elute viable healthy cells or diseased cells. In certain embodiments, cells can be captured using an aptamer specific to a cell surface marker. Aptamers can be single- or double-stranded RNA or DNA oligonucleotides. Aptamer sequences can be determined using Systematic Evolution of Ligands by Exponential Enrichment (SELEX) or other selection processes (see for example Base Pair BioTechnologies, Inc., Houston, Tex.). The aptamers can contain non-standard or modified bases. As used herein, a "modified base" may include a relatively simple modification to a natural nucleic acid residue, which modification confers a change in the physical properties of the nucleic acid residue. Such modifications include, but are not limited to, modifications at the 5-position of pyrimidines, substitution with hydrophobic groups, e.g., benzyl, iso-butyl, indole, or napthylmethyl, or substitution with hydrophilic groups, e.g., quaternary amine or guanidinium, or more "neutral" groups, e.g., imidazole and the like. Additional modifications may be present in the ribose ring, e.g., 2'-position, such as 2'-amino (2'-$NH_2$) and 2'-fluoro (2'-F), or the phosphodiester backbone, e.g., phosphorothioates or methyl phosphonates.

Aptamers have been shown to be capable of cell capture. For example, Shen et al. captured CTCs using DNA aptamer-functionalized silicon nanowires to capture and release non-small cell lung cancer cells (Shen, et al. Advanced Materials, Volume 25, Issue 16, pages 2368-2373, Apr. 24, 2013). Wan et al. captured CTCs using aptamer functionalized glass beads. The cells were released using a combination of soft shaking and anti-sense RNA (Wan et al, Lab Chip, 2012, 12, 4693-4701).

Figure 8:
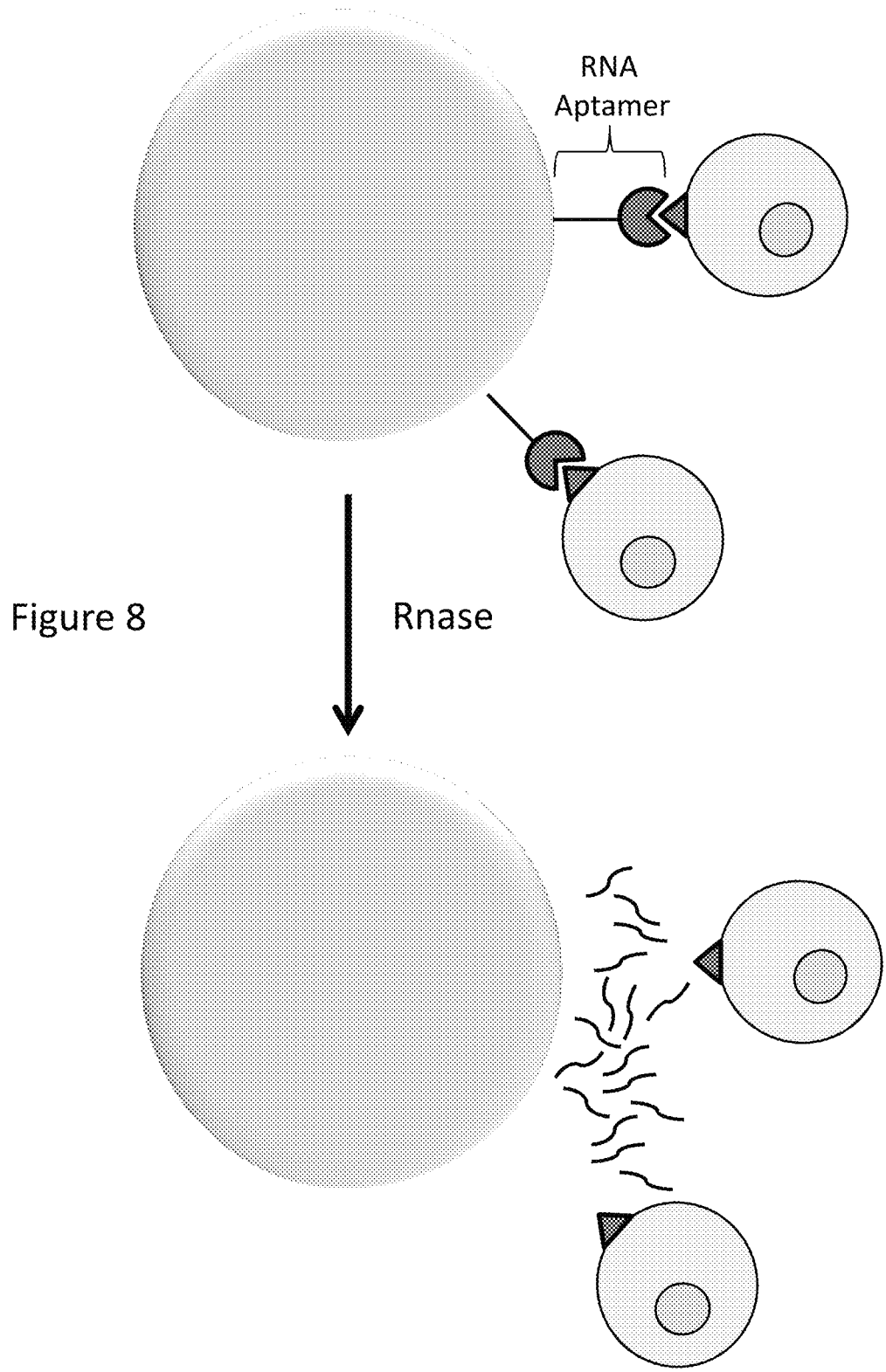
FIG. 8 is a depiction of an embodiment of an aptamer capture and release strategy.
Figure 9:
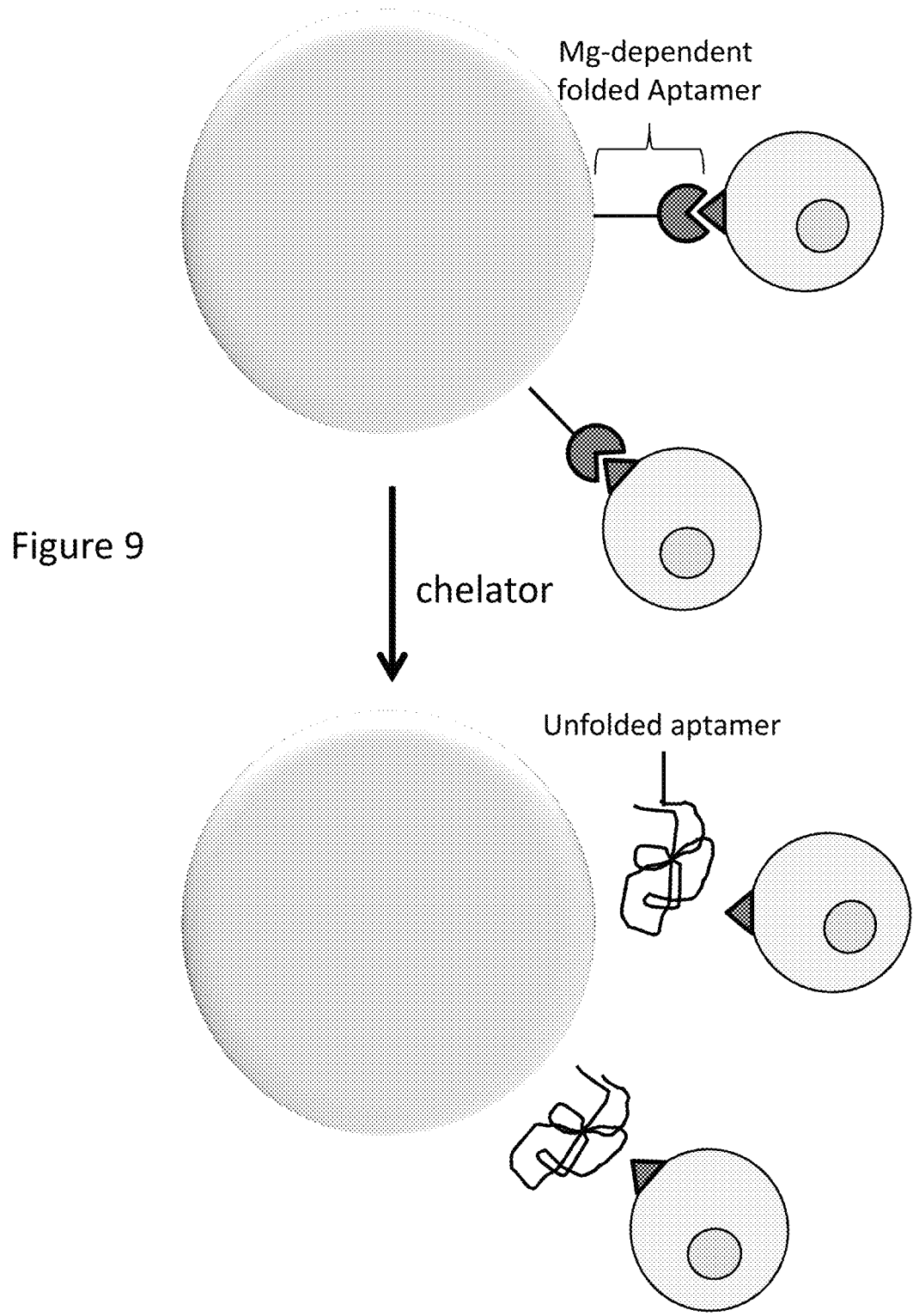
FIG. 9 is a depiction of an alternate embodiment of an aptamer capture and release strategy.

Aptamers can be chemically conjugated to chromatographic beads. For example, see Zhou et al., Trends in Analytical Chemistry. 2012 41:46-57. Alternatively, biotin-labeled aptamers could bind streptavidin resin. Cell elution can be performed by a means with disrupts the aptamer or the aptamer-cell bond. For example, RNase could be used to perform elution from an RNA-based aptamer as shown in FIG. 8. Other elution strategies that can be employed with aptamers are anti-sense, photocleavage (at an appropriate wavelength), use of an enzyme or chemical cleavage. An aptamer comprised of a disulfide bond could be treated with a reducing agent to disrupt the bond and release a bound cell. An aptamer containing a magnesium-dependent fold could unfold and release a bound cell with the addition of a chelator as shown in FIG. 9.

The eluent can be passed through the column by any means described above for the sample. The elution step may be repeated once to several times. In certain embodiments, the eluent is incubated on the column for a period of time to increase the efficiency of cell elution. After the purified cells are eluted from the column, they can be analyzed by any means desired.

In certain embodiments, the cells are not eluted but instead are manipulated or interrogated on the column. The cells can be labeled on column, for example with a fluorescent antibody or aptamer. Cells can be lysed on column and cell components (e.g., nucleic acids) can be eluted and analyzed.

It can be important to purify cells rapidly to maintain viability. Isolation of cells can be performed remarkably fast using the columns and methods of the invention. Cells can be isolated in less than 3 hours, less than 2½ hours, less than 2 hours, less than 90 minutes, less than 75 minutes, less than 60 minutes, less than 50 minutes, less than 45 minutes, less than 40 minutes, less than 35 minutes, less than 30 minutes, less than 30 minutes, less than 25 minutes, less than 20 minutes, less than 15 minutes or less than 10 minutes. In other embodiments, cell purification can take longer, particularly when viability is not as important.

In some embodiments, the resin with cells attached can be removed from the column after the capture and wash steps. In these embodiments, the resin (with cells attached) can be placed in a well. Cell lysis can be performed if desired. PCR can be performed either on whole cells or lysed cells. Nucleic acids can be isolated and analyzed e.g., by sequencing.

Figure 10:
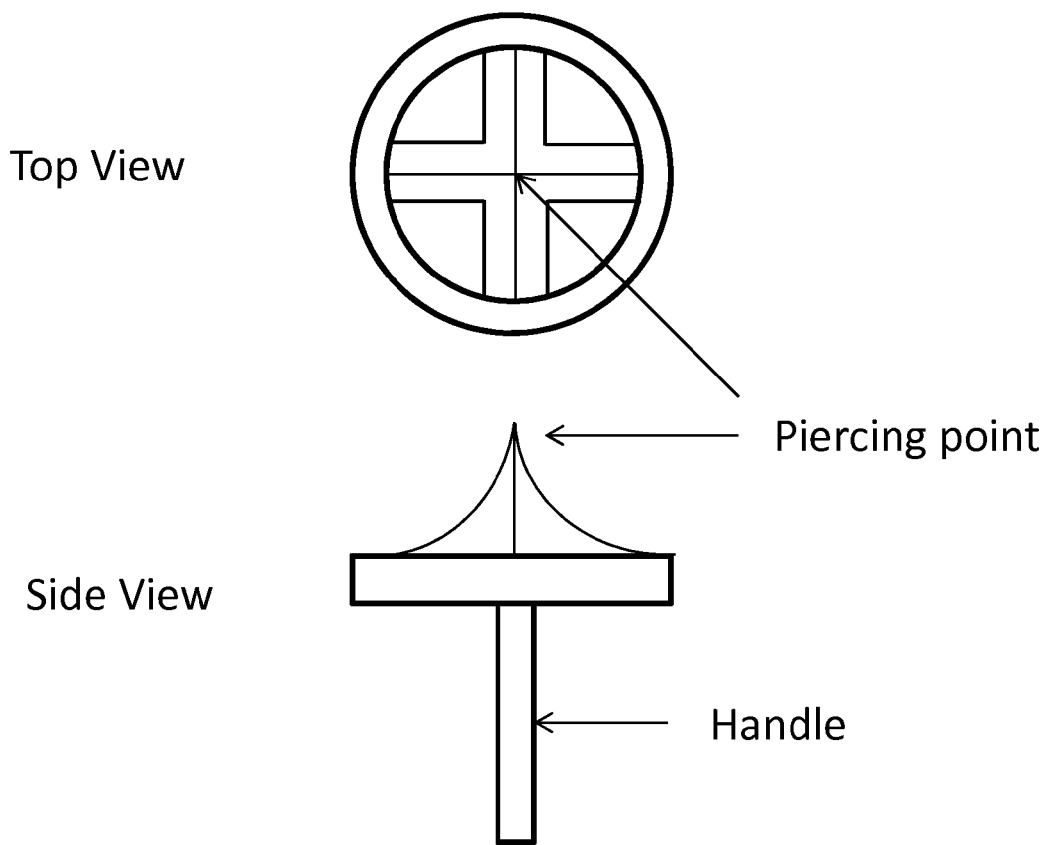
FIG. 10 is a depiction of one embodiment of a frit-piercing tool.

Removal of the resin can be performed by piercing the bottom frit of the column and then pushing the resin into a well with air or liquid. One embodiment of a frit piercing tool is shown in FIG. 10. The frit piercing tool is not limited to the geometry shown in FIG. 10; a variety of geometries are possible. The tool can be used manually by grasping the handle and pushing the piercing point of the tool into the column bed. Then the tool is removed and the column is placed above a tube or microplate well which will receive the resin. Air or liquid can be used to push the resin into the well.

In another embodiment, the frit piercing tool can be recessed in a well, handle side down into the well of a microplate. The column is positioned above the well and pushed down into the well to pierce the frit. The piercing tool can be removed or remain in the well. Air or liquid can be used to push the resin into the well.

Because the columns are packed to minimize cell trapping, they can be very efficient in isolating the desired cell type. It is possible to capture at least 80%, at least 85%, at least 90% or at least 95% of the desired cells from a particular sample.

After cells are isolated, an assay may be performed to determine cell viability or to count the number of viable cells.

During and after cell isolation, it is necessary to maintain conditions that promote cell viability. It may be necessary to use the proper media and maintain the proper osmolarity even in the sample, wash and elution solutions. For example, viable cells can be stored in sterile buffers such as phosphate buffered saline (Ca/Mg++ free) or HEPES (N-2-hydroxyethylpiperazine-N'-2-ethanesulfonic acid) or others known in the art. These buffers can contain EDTA, HBSS (Hank's balanced salt solution), heat-inactivated fetal bovine serum and other constituents. One reference for such media from the UCSF Cell Culture Facility can be found on their website.

Large Column Operation

Large columns are defined herein as those columns having a bed size greater than 100 μl and a capacity between 2 mL and 100 mL. In some embodiments, large columns can be pipette tip columns while in other embodiments, the large columns are not pipette tip columns. Large columns that are not pipette tip columns have a body and bed volume of 1-100 ml.

Larger columns of the invention have a number of different properties from the smaller columns. It is not simply a matter of scaling up small columns to produce large body affinity columns. First, larger columns can have a different geometry than the smaller columns. Specifically, the ratio of the column diameter to the rein bed height can be greater in the large columns.

Second, it is possible to use smaller liquid volumes relative to the bed volume. For example, in the smaller, previously-described columns a minimum of 2 bed volumes could be aspirated. But in the larger columns, it is possible to aspirate one bed volume of liquid.

Furthermore, higher flow rates can be used with the larger columns. Columns that have a body size of at least 2 mL and a bed volume in the range of 200 μL to 50 mL can be operated using significantly faster flow rates than columns having a smaller column body and bed volume. Flow rates in the range 1 ml/min to 12 ml/min and faster can be used. In large column embodiments, the flow rate for passing liquids through the column can be within a range having a lower limit of 0.5 ml/min, 1 ml/min, 1.5 ml/min, 2 ml/min, 2.5 ml/min, 3 ml/min, 3.5 ml/min, 4 ml/min, 4.5 ml/min, 5 ml/min, 6.5 ml/min, 7 ml/min, 7.5 ml/min, 8 ml/min, 8.5 ml/min, 9 ml/min, 9.5 ml/min, 10 ml/min, 10.5 ml/min, 11 ml/min, 11.5 ml/min, 12 ml/min or greater. The upper limit of the flow rate can be in the range of 60 ml/min, 70 ml/min, 80 ml/min, 90 ml/min, 95 ml/min or 100 ml/min.

As a result of the higher flow rates, the separation times are shorter; cells can be isolated and recovered in a very short time. In some embodiments, cells can be isolated from a biological sample in less than 45 minutes, less than 30 minutes, less than 25 minutes, less than 20 minutes, less than 15 minutes, less than 10 minutes or even less than 5 minutes.

Figure 11:
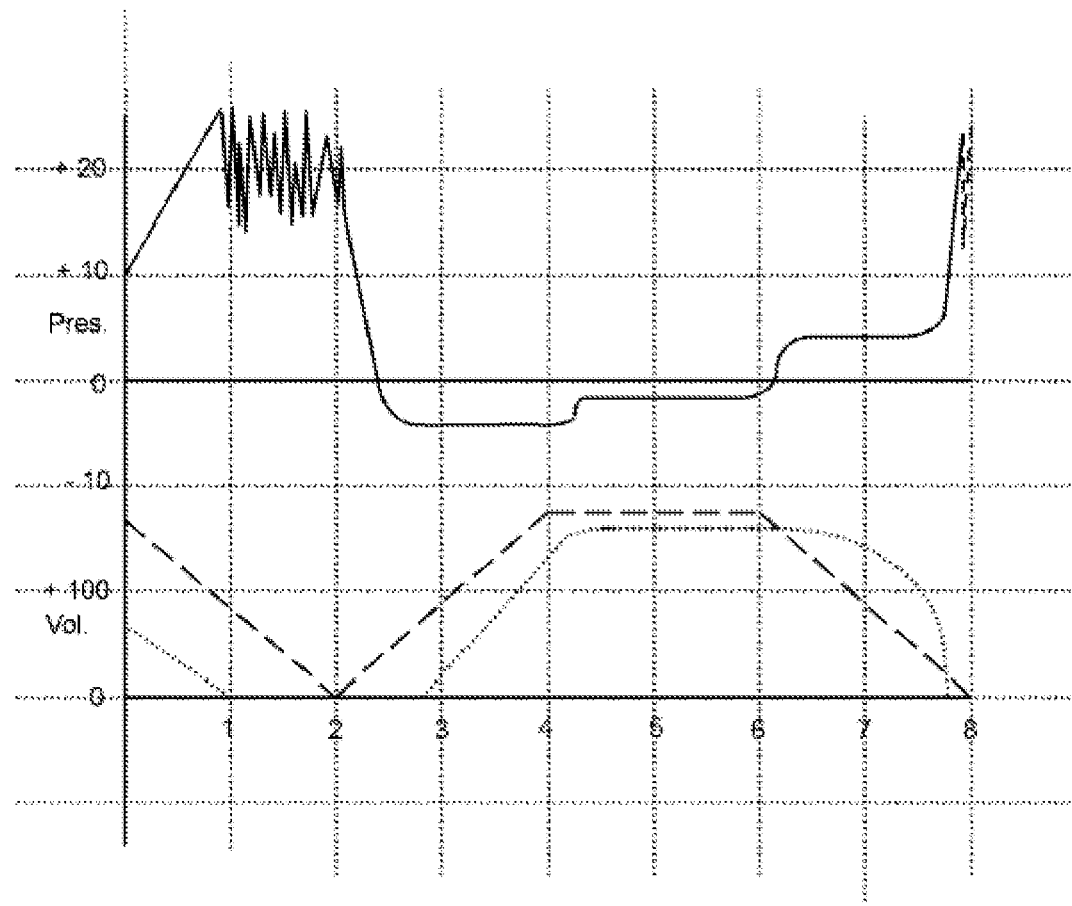
FIG. 11 plots the head pressure of a pipette tip column, the chamber volume of a syringe attached to the pipette tip column, and the volume of liquid in the column, all as a function of time, during a typical extraction process.
Figure 16:
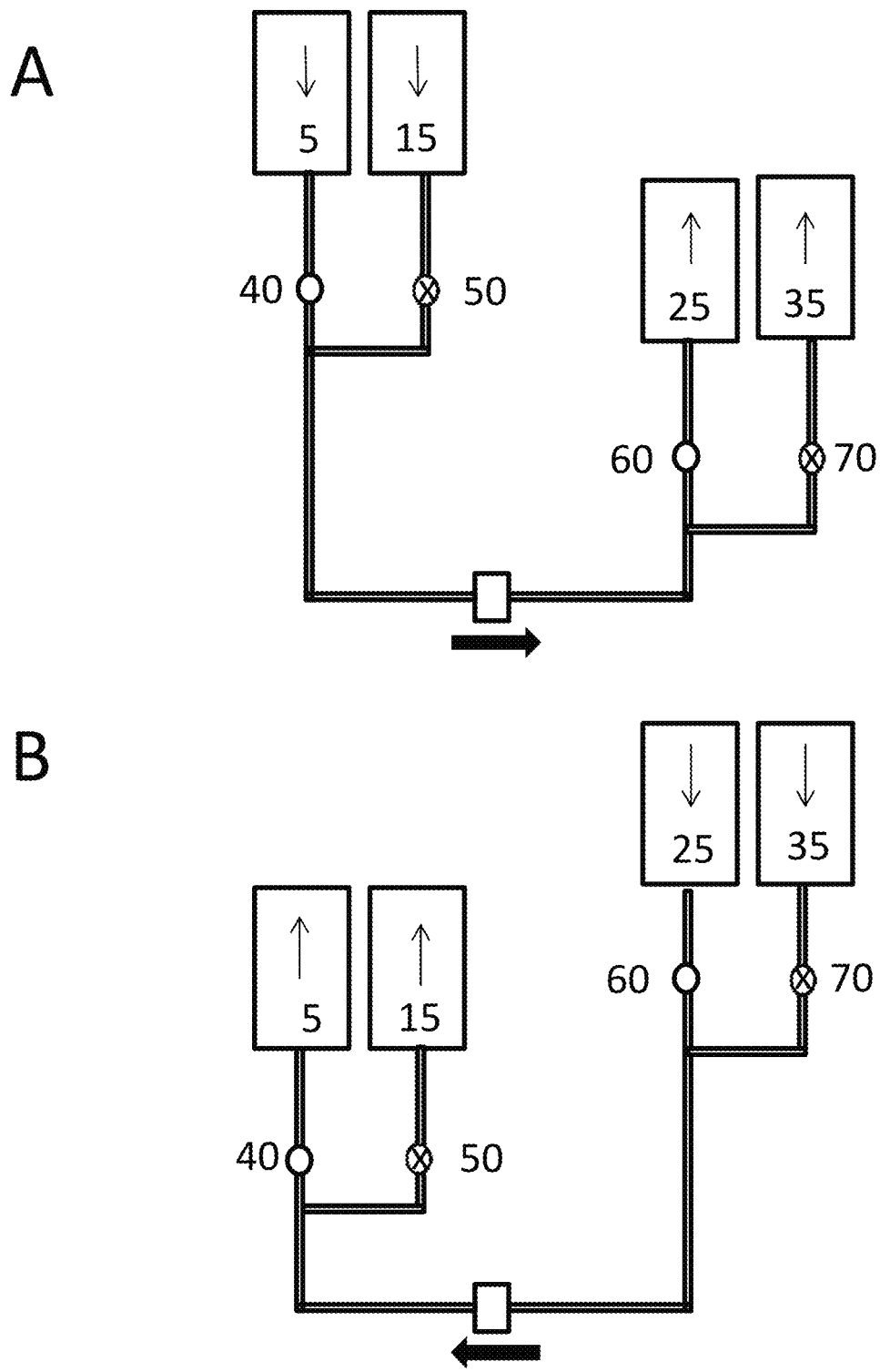
FIG. 16 depicts an embodiment of a closed chromatography column system for capture of cells with a back and forth flowing system with five each feed and receiving containers on each side of two option closed system columns.

FIG. 16 from U.S. Pat. No. 7,837,871 shows that when smaller columns up to 1 mL body size that have affinity resins with the interstitial liquid filled with a liquid are inserted onto a pump a position head pressure is produced. FIG. 16 is reproduced herein as FIG. 11 for illustrative purposes. Head pressure is the pressure inside the column body above the column bed that results from insertion of the pipette pump onto the column or pipette tip column. The pressure is positive due to the sealing of the column body pump interface as the pipette is inserted onto the tip and when air cannot or will not escape through the bed of the column. In many cases, due to this positive pressure, air cannot travel through the column bed because air cannot pass through the frit and/or the bed contains interstitial liquid between the packing, preventing the passage of air. In order to make these columns operate, after insertion of the pump, the pump piston displacement on the intake must be programmed to be more than the liquid desired to flow through the column. However, it was discovered that when large body columns were used, the piston offset used with the smaller columns to equalize the positive pressure did not work. The piston offset used for the smaller columns did not allow processing of liquids through the column, especially on the intake but also upon expulsion. Referring to FIG. 11, the large columns of the invention have a pressure of between 0 and 10 inches of water (0-0.4 psi) at time 0.

In the larger columns of the invention, the pressure generated upon insertion of the pump into the column is 0.4 psi or less. In some embodiments, the head pressure is less than 0.3 psi, less than 0.2 psi, less than 0.1 psi or less than 0.05 psi. This low head pressure allows back and forth flow that corresponds with the piston movement and not to the head pressure, as was observed in FIG. 11.

When using the smaller pipette tip columns described previously (e.g., in U.S. Pat. No. 7,837,871) with back and forth flow, a pause was needed between the between pumping strokes. These pauses are necessary to the operation of the column. Failure to do so results in the fluid not flowing entirely through the column. It was necessary to pause for a minimum of 10 seconds and as long as 30 seconds or even 1 minute after each aspiration or expulsion. This phenomenon was described in U.S. Pat. No. 7,837,871 (see FIG. 11 herein). This pause allows the fluid flow to catch up with the pump piston position. With the larger columns, pause times of less than 10 seconds, less than 5 seconds and even no pause at all has been discovered to be possible. These shorter pause times additionally contribute to the very short cell isolation times possible with the large columns.

On-Column Lysis or Interrogation

In some embodiments, the cells are not eluted from the column. Instead, they can be lysed on column or the column bed material with cells bound can be released from the column and subjected to further analysis such as a polymerase chain reaction. Nucleic acids, DNA or RNA associated within with the cells or that have bound to the cells or released from the cells may be measured.

In some cases it is desirable to label cells on the column for instance with an antibody, fluorescent tag or aptamer. On-column labeling can be useful for diagnostic applications by enhancing the signal to noise ratio.

Cells captured on the column can be interrogated with groups of compounds to identify those that bind cells with the desired affinity. For instance, a library of compounds can be added to the column to determine which materials in the library have an affinity for the cells on the column. The sample containing the library is added to the column. The column is washed. The stringency of the wash may be varied and controlled to allow or enhance capture of library materials. Then the column is washed with a high stringency material to elute the compounds or the cells with compounds attached are eluted from the column. Analysis to determine the identity of the compounds may be performed with mass spectrometry. The concentration of the various compounds may indicate the ability of the cells to capture a particular compound. The concentration of the compounds recovered may be determined by liquid chromatography or mass spectrometry methods.

In some embodiments, the columns of the invention can be used to distinguish live and dead cells. Reagents sold by Life Technologies and others can be useful for these methods.

Cell Therapy

The invention additionally includes devices and methods for treating diseases. In some embodiments healthy cells are transferred between organisms. For example, donor cells from a healthy pancreas can be isolated on a column and transplanted into a patient suffering from Type 1 Diabetes. Stem cells are used for bone marrow transplantation a will likely have a variety of therapeutic applications in the future.

Samples containing donor cells can be obtained from a variety of sources including human, animal and cell culture. For example, donor cells can be obtained from cell culture, body fluids such as blood or lymph, organ tissue, bone marrow, etc. Donor cells can be engineered cells.

In other embodiments, cells are used to deliver gene therapies. Genes can be introduced into cells for example, by using a replication-defective adenovirus to produce engineered cells. These cells can perform a variety of therapeutic tasks such as delivering drugs, destroying cancer or regulating the immune system.

In one study, T cells were engineered to produce antibodies that bind cancerous cells (Grupp et al., N Engl J Med. 2013 Apr. 18; 368(16):1509-18). These engineered T cells were introduced into patients with leukemia to achieve remission or tumor size reduction. In this type of application, patients' T cells could be isolated using a column of the invention, engineered and then proliferated in cell culture. After the engineered T cells were grown, they could be isolated with a sterile column prior to introduction into a patient.

The columns and methods of the invention can be used to isolate cells used for cell-based therapy. In these embodiments, sterile columns can be used for cell isolation. One advantage to this approach is that the cell populations obtained will be free of contaminants. In certain embodiments, cells isolated from columns are administered to patients to treat diseases such as cancer, diabetes, heart disease, Parkinson's, Alzheimer's, liver disease and others. Healthy cells can be used to replace cells in damaged or disease organs. Cells isolated from any source can also be transferred to a different individual or organism. For instance, cells can be transferred to a mouse or other animal model for research purposes.

Therapeutics Screening

Columns and methods of the invention can be used to screen drug leads and identify drug targets. Cells can be immobilized on the column medium and challenged with pools of drug candidates such as small molecules, engineered proteins (such as an engineered T-cell receptor), biologics or other entities. The column can be washed to remove species not tightly bound.

At this stage, the cells bound to drug candidates can be interrogated. Different solvent conditions can be applied to the column to test binding and dissociation conditions. Alternatively, cells bound to a drug candidate or other entity can be released from the column and studied. For example, cells can be disrupted to create membrane fragments consisting of cell surface components bound to drug targets. The drug targets and the drug leads can be identified using methods such as mass spectrometry.

Alternatively, drug candidates can be immobilized on a column and different cell types can be passed through the column to identify and then characterize interaction. In some embodiments, cells can be manipulated prior to passing them through the column. For example, cells can be mixed with a drug candidate and subjected to competition experiments with other drug candidates present on the column.

Cell Clean-Up

The columns and methods described herein can additionally be used for cell clean-up. For instance, it can be desirable to separate cells from contaminants, collect materials from cell populations or perform buffer exchange. Existing methods for cell clean-up include magnetic beads, dialysis and centrifugation which are time-consuming, single equilibrium procedures. The columns and methods of the invention provide a rapid alternative and offer the advantage of being a multi-equilibrium process.

In some embodiments, cells are purified away from contaminants by capturing contaminants on the column while cells pass through unencumbered. Contaminants can be captured on the solid phase using for example, an affinity group, aptamer capture, ion exchange or other strategies. Alternatively, size exclusion can be used to separate cells from contaminants. Using size exclusion, cells might pass through the column quickly while smaller contaminating molecules might enter the solid phase which would cause them to pass through the column more slowly.

Diagnostics

Some requirements of a good diagnostic are listed below.

Rapid

Simple

Enrich sample

Low background signal

Remove materials that give signal

High detection signal

Linear signal to sample concentration relationship

The columns and methods of the invention can be used for a number of diagnostic applications including oncology, virology and infectious diseases. Diagnostic applications include isolation of any cell type and the option of additional cell characterization on column or post column. One application is the identification of pathogens such as viruses, bacteria, fungi and protozoa from a patient sample. Another application is the isolation and characterization of cancer cells, such as circulating tumor cells (CTCs) as described below in Example 3. Isolation of CTCs is useful for early cancer detection, characterization of tumor cells, monitoring disease treatment, progression or remission.

Diagnostic applications of the invention can be used in a variety of settings. In certain embodiments, diagnostics are utilized in a research setting such as academia, biotechnology or pharmaceutical company. In other embodiments, the columns and methods of the invention can be used in point of care settings including emergency rooms, intensive-care units, patients' bedsides, physician's offices, pharmacies and blood banks. In still other embodiments, diagnostic applications can comprise in-home tests.

Diagnostic target cells can be any cell type listed above. As described above, cells are not defined herein as limited to entities capable of self-replication. Included in the definition of cells are viruses, parasites and exosomes and organelles. A non-limiting list of diagnostic targets include mammalian cells, human cells, cancer cells, circulating tumor cells, viruses, bacteria fungi and parasites. A non-limiting list follows: *Shigella, Salmonella, E. coli, Helicobacter pylori, Campylobacter, Chlamydia, Gonococcus, Streptococcus, Staphlococcus, Mycoplasma, Trichomonas vaginalis, Clostridium botulinum*, HIV, Hepatitis A, B and C, Herpes, Amoeba/parasites, *Entamoeba histolytica*, Acanthamoeba and Naegleria, Cryptosporidium, Giardia, Fungi such as Coccidiodomycosis (Valley Fever), blastomycosis, histoplasmosis, yeast—*Candida albicans* and other *Candida* sp. (hospital infections, blood infections) and opportunistic pathogens such as Cryptococcosis and Aspergillosis.

Although it is not required for all diagnostic applications, a label can be employed. For example, cells can be captured and then labelled on the column. Alternatively, cells can be labelled prior to column capture. When cells are labelled prior to capture, the label can aid in cell capture. In some embodiments, the label can actually be the entity captured on the column. Labelled cells captured on the column can be washed, eluted and a detection step performed. In another embodiment, cells can be labelled following elution from the column. An advantage to this approach is that a homogeneous cell population can be obtained prior to the labelling step.

A label is defined herein as any entity that can aid detection. A variety of labels can be used for this purpose. For example a dye-labelled antibody or Fab can be used. In addition, an antibody or Fab can be conjugated with any kind of tag that aids detection. In addition to dyes, non-limiting examples of tags include radioactive labels, proteins, enzymes (e.g., horse radish peroxidase), and metals including rare earth metals. Labels are not limited to tagged antibodies or Fabs; they include anything that can bind the cell surface such as a protein, a dye or other molecule.

Dye labelled antibodies or Fabs can used to label specific cell surface markers and viable/dead cells. Dyes used to label proteins include Ellman's Reagent, Coomassie Blue, Lowry reagents and Sanger's reagent.

Post-column label detection can be carried out using a number of different methods. For instance, detection can be done with flow cytometry, a microscopy, a spectrophotometry, a colorimetric reader, a protein assay or a nucleic acid assay.

In alternate embodiments, on-column detection can be utilized. On-column detection can be performed for example, by reflectance (UV or visible), fluorescence, colorimetric detection (e.g., ELISA), chemiluminescence and others.

Cell Based Stationary Phase for Liquid Chromatography

Columns of the invention can be used to produce and use a stationary phase of cells bonded to a substrate for use in liquid chromatography. The cell stationary phase may be comprised of live or active cells. Samples are injected into mobile phase and enter the column. The interactions of the sample with the cell based stationary phase are identified and measured. Retention data and column interaction data are collected and analyzed. In most cases, the liquid phase flow through the column is unidirectional. In some cases, a bi-directional flow column may be employed. Applications of cell based stationary phase liquid chromatography include drug discovery, drug development, and cell research. In drug discovery, the interaction of a library of compounds may be studied for a particular type of cell. In drug development, the interaction of a particular drug candidate, class of drug candidates, or analogs of a drug candidate may be studied. In cell research, the interaction of a compound with a particular cell or component of a cell may be measured and studied.

The column containing the cell stationary phase can be constructed several different ways. In one procedure, the cells are attached to the surface column packing resin and then the resin containing the cell stationary phase is packed into a column producing the cell based stationary phase. Prior to packing, the cells are attached to the resin substrate as slurry. This also can be accomplished in two ways. The cells may be activated with an antibody or other chemical entity that in turn can attach to the resin. The cells are introduced into the resin and the cells attach to the substrate producing the cell stationary phase. Or, the resin substrate may be activated with an antibody or other chemical entity that can in turn attach the cells. The cells are introduced into the resin and the cells attach to the substrate producing the cell stationary phase. Once the cell stationary phase is produced, the resin is packed into the column.

Resins are activated to be able to capture cells to make a cell stationary phase. One example of this is to load an antibody onto a Protein A column resin beads. The antibody is selective for surface proteins on the cells. Or cells can be activated to be able to attach to resin beads. One example of this is to attach a His-tagged FAB to cells. Then after removing excess FAB material by centrifugation, the cells are introduced to an IMAC resin bead. The cells attach to the beads through the His-tagged FAB.

In another procedure, the resin substrate (not containing the cells) is packed into a column. The resin bead substrate contains an affinity group that can capture cells. This capture step can be accomplished in several ways. For example, the cells may be activated with an antibody or other chemical entity that in turn, can attach to the resin. The cells are introduced into the column and the cells attach to the substrate producing the cell stationary phase. Or, the resin substrate may be activated with an antibody or other chemical entity that can in turn, attach the cells. The cells can be introduced into the column and the cells attach to the substrate producing the cell stationary phase. The types of substrate used to form the cell based stationary phase include affinity and ion exchange resins.

In order to produce the cell stationary phase columns, the column and substrate must have the same cell accessibility characteristics as columns used to capture and purify cells. That is, the cells are accessible to chemical interactions. Cells are not trapped in dead spaces and cells are not damaged by the frits or resin. The cell stationary phase columns are characterized by low backpressure, low dead volume, and very little dead space.

Cells attached to affinity resins packed into a chromatographic bed have surface groups of various types that can be employed to produce the stationary phase interaction mechanism. These groups include proteins including glycoproteins, lipids, sugars and other groups. Analytes such as drug candidates can interact with these groups by pumping them or injecting them into a liquid phase flowing through columns. This interaction can be measured in different ways, depending on how the chromatography is performed and the kinetic rate constants of the on/off interaction of the cells with the stationary phase.

Once the cell stationary phase column is prepared, chromatography can be performed. Cells have surface groups that can interact with analytes that are injected or added to the liquid phase. Frontal or break-through chromatography, displacement chromatography or partitioning chromatography can be performed. In one example, a column was prepared by gluing a frit on one end, packing the column and then gluing a second frit on the top of the column. A 37-micron pore, 60 micron thick Nitex screen frit was attached to the end of an acrylic tube 0.750 inches long, 0.500 inch outer diameter and 0.375 inch inner diameter. Packing was accomplished by standing the column on a stand with deep-well plate beneath the column that allowed liquid to flow out of the lower end. An aqueous slurry of agarose resin, 45-165 micron particle size, was transferred to the column by pipette. The packing material was not compressed. Excess liquid drained away filling the column with resin. Additional slurry was added until the bed of the column reached the top of the column. A Nitex screen of the same material used for the other frit was glued onto the column end using a methylene chloride solvent.

Figure 12:
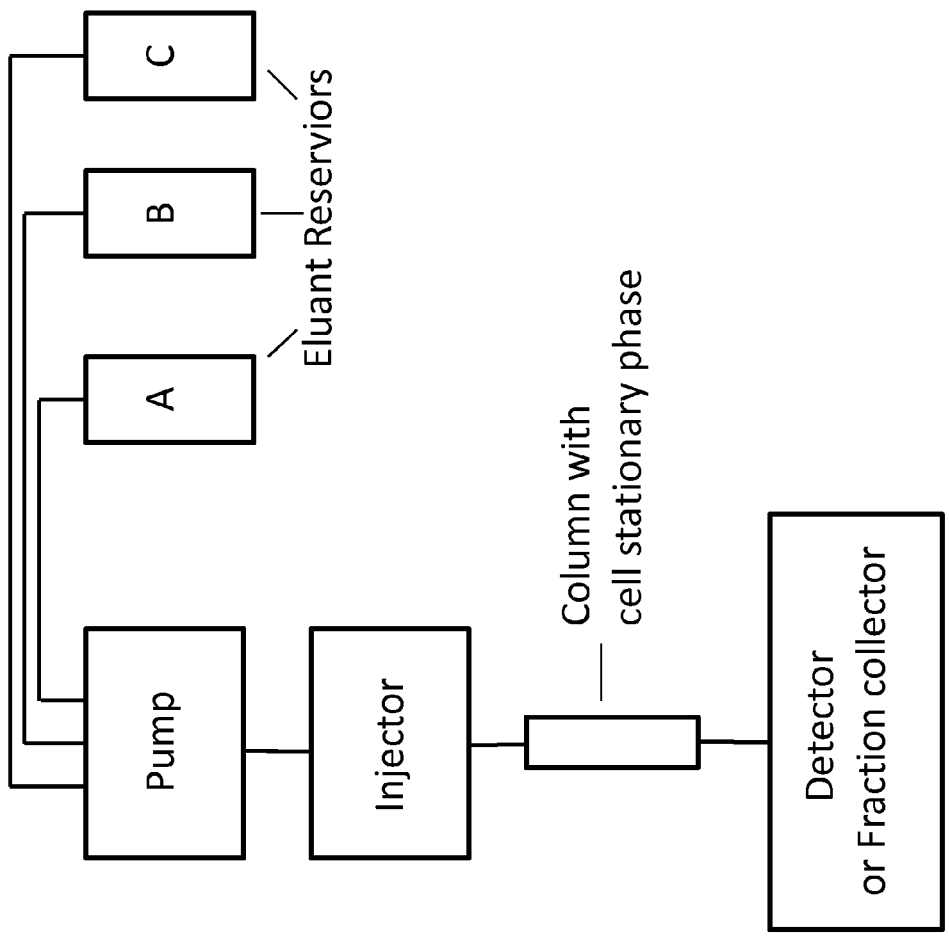
FIG. 12 is a depiction of one embodiment of a column having a cell stationary phase.

Silicone tape was wrapped round the column to increase the diameter. Then, two 10 mL plastic syringe bodies and male luer connections were cut to the 1 mL volume mark and placed on the end of the column. The column body was wrapped with stretchable silicone tape to seal the column body. Male luer connections were connected to the inside of clear flexible Tygon tubing 250 inch outer diameter to connect to the injector and fraction collector. This system is shown in FIG. 12.

In a second example, the cells are attached to the column. A His-tagged FAB is pumped through the column loading the column completely with the FAB. The FAB is selective for a surface protein on the HeLa cancer cell line. After washing the column, HeLa cells are pumped into the column loading cells onto the surface of the stationary phase. The column now contains a HeLa cell-based stationary phase.

Generally, the cells on the cell based stationary phase are alive and active. Cells contain surface groups including proteins, carbohydrates, sugars, lipids, etc. The proteins may contain phospho groups, glycans, etc. Interactions between cell surface groups and other entities can be examined. For example, antibodies, FABS interactions with cell surface groups, enzymatic interaction with cell surface groups, nucleic interaction with proteins or other groups, ion exchange interaction with phospho groups, etc.

The interactions may be additive. For example calcium may add to membrane channels. In this case, the kinetic rate of uptake would be higher than release and breakthrough curve measurement may be more appropriate.

The interaction of different materials with the stationary phase is measured using various chromatographic techniques. The extent of interaction under different conditions may be measured. The identity of materials interacting may be determined. This measurement may be relative compared to the eluent or entity in the eluent or may relative compared to another analyte.

Depending on the kinetic rate of interaction, the chromatography can take different forms. For rapid kinetic interaction, partitioning chromatography may be performed. Measurement of interactions may be retention time or capacity factor. Displacement chromatography may be performed. Measurement may be by the ability of an analyte to displace or be displaced from a stationary phase. Frontal or breakthrough chromatography may also be performed.

For slow kinetic interactions, displacement and breakthrough chromatography may be used. The mobile phase flow rate and the linear flow velocity may be adjusted (lower) if necessary so that the interactions may be measured.

Partitioning and breakthrough chromatography is performed with unidirectional mobile phase flow. Displacement chromatography mobile phase flow is either unidirectional and bidirectional flow.

Breakthrough curves measure effective capacity for a particular analyte, the kinetics of on interaction and the kinetics of off interaction. Pumps, injection, detection is the same as other types of liquid chromatography although the columns are generally low backpressure.

Partitioning chromatography requires tight injection if partitioning is rapid and the isotherm describing the analyte interaction with the column is sharp. But generally larger injection volumes can be employed. Breakthrough chromatography requires a continuous uniform (injection) supply of analyte. Injection is at the top or inlet of the column for partitioning or displacement chromatography. Displacement chromatography generally requires a large injection ensuring that the stationary groups are displaced with the eluent. Injection can be at the top of the column or at the bottom of the column for back and forth flow.

Figure 13:
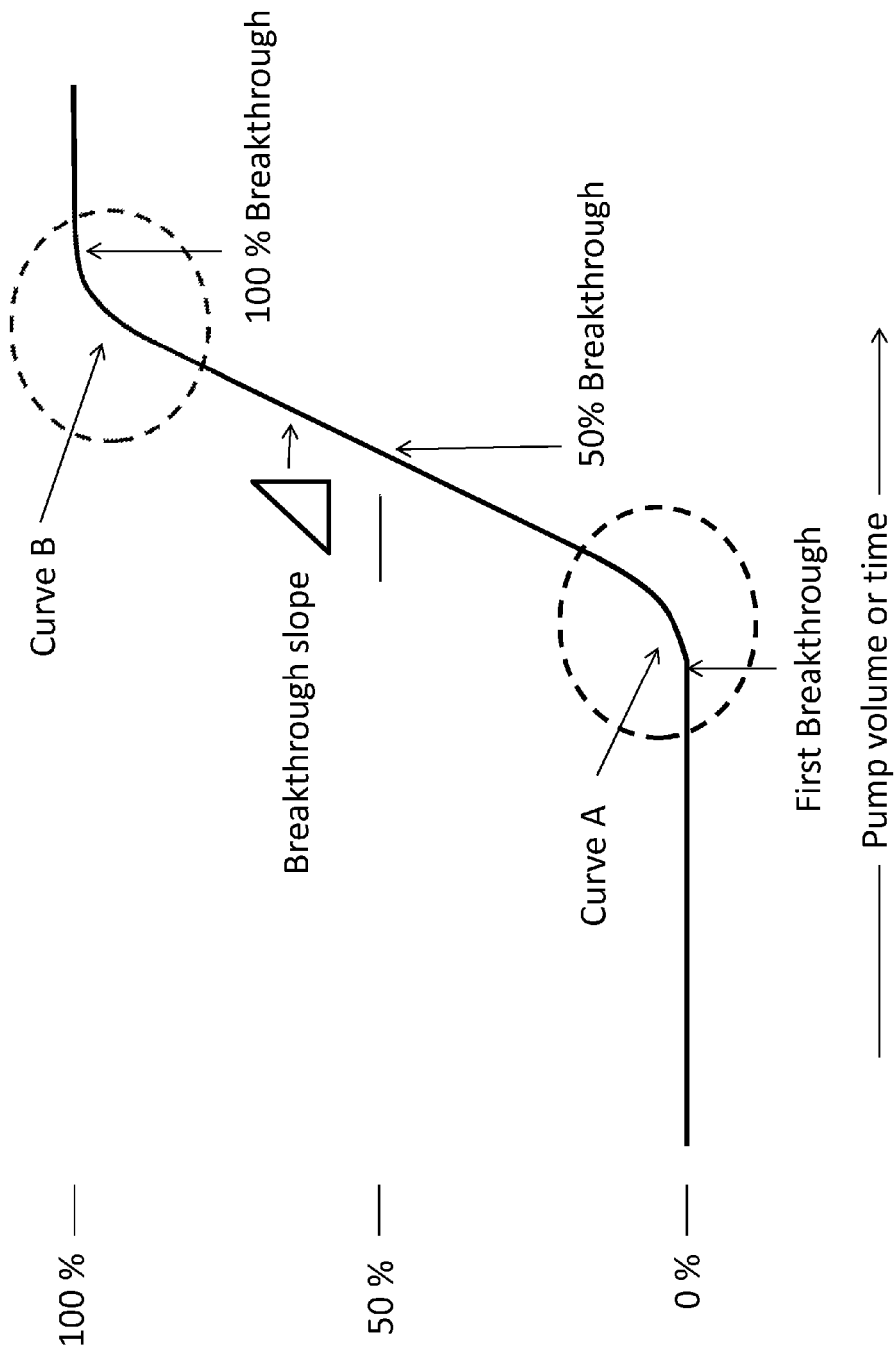
FIG. 13 shows the features of a curve obtained from breakthrough chromatography.

Detection may be continuous or fractions may be collected and analyzed. Analyte measurements include retention time, capacity factor, selectivity coefficient, breakthrough curve parameters. The geometry of a breakthrough curve is depicted in FIG. 13. The x-axis denotes the time the analyte is pumped or the volume of the analyte pumped. The y-axis shows the amount of analyte that exits the column relative the column input concentration. To start, analyte is pumped through the column and is taken up by the stationary phase. The first breakthrough is where the analyte is not completely taken up from the column. The curvature of slope A is an indication how fast the analyte is taken up by the stationary phase. A long extended slope of curve A indicates a slow on-rate of the analyte. The slope of the breakthrough is an indication of the kinetics of uptake and release and of how the column is packed. An ideal breakthrough is vertical, but in practice, all breakthrough curves have a slope. The 50% breakthrough point shows how much analyte is taken up by the column. This is calculated by multiplying the volume of the 50% breakthrough point times the concentration of the analyte being pumped through the column. Curve B is the curve leading into the point where no analyte is being taken up by the column, 100% breakthrough. A long extended curve at this point indicates a slow off-rate and/or a slow on rate of the analyte.

Competing materials can be added while performing breakthrough chromatography. Generally, resin beads with small diameters packed in columns with low dead volume will give breakthrough curves with steeper slopes. In these cases, the mass transfer and diffusion to the surface of the bead are decreased so that the kinetic interaction and the extent of interaction are measured.

Liquid chromatography employing cell based stationary phases can be used for research in drug discovery, drug development, cell biology research, protein-protein interaction research, cell-cell interaction research, enzymatic research and other types of research or clinical applications.

Drug Development

The cell based stationary phase can be used for drug development applications. In some embodiments, cells can be immobilized on a column and then challenged with different entities such as libraries or pools of molecules (e.g., small molecule drug leads or biologics). In other embodiments, cells can be immobilized on a column and the interaction with other cells can be examined. Conversely, drug candidates can be immobilized on the column and challenged with different cell types.

In one example, a library of small molecule drug candidates labeled for identification can be exposed to cells immobilized on a column. A wash step can be performed and the cells can be eluted from the column. Those cells that have a drug candidate bound can be identified. Mass spectrometry can be used to identify the drug candidate and its target on the cell.

A number of techniques can be used to screen for potential drug leads. As mentioned previously, target cells can be immobilized on a column. When done in multiplex, multiple cell-immobilized columns can be screened in parallel. Multiplex operation can be performed with between 2 and 1536 columns simultaneously. Each column can be subjected to a different drug lead to screen for the desired cell signaling event. The following techniques can be used.

1. Eluting the cells and performing qPCR (e.g., to measure a change in gene expression or particular mRNA). For example, expression of genes involved in programmed cell death could be measured.
2. Use cells transfected with a reporter gene such as GFP or luciferase. The reporter gene would be engineered with a promoter region corresponding to the desired cellular event. If the promoter is induced by a drug lead, the cell would express the reporter and this would be detectable on column. Detection of the reporter gene expression can be performed on column or after cells are eluted from the column. As an example, differentiation of stem cells could be measure with a reporter gene.
3. lithe drug is designed to induce a regenerative cellular event, cell growth and doubling can be monitored as the final assay. Cells could be eluted and grown in cell culture.

In one example, cells having a known drug target could be used to identify potential drug as follows.
   Put cells having a validated target on the column
   Challenge with library of fluorescently-labeled drug candidates
   Wash
   Elute cells
   Count/separate labeled cells in cell sorter
   Analyze by mass spectrometry As an alternative to fluorescent labels, drug candidates could be labeled with DNA barcodes. PCR could then be used to identify particular candidates able to bind cells.

In another example, an unlabeled library can be used and drug candidates can be identified using a cell viability assay.
   Put cells having a validated target on the column
   Challenge with library of drug candidates
   Wash
   Add live/dead cell stain on column
   Wash
   Elute cells Alternatively, the cells can be stained after elution. The results could be evaluated using fluorescence microscopy or flow cytometry. A column in which the cells were not challenged with the drug candidate could serve as a negative control.

A variety of detection methods can be applied to the methods described herein. Non-limiting examples follow.
   cell sorter or flow cytometry
   fluorescence microscopy
   light microscopy (e.g., to examine viability or morphology)
   mass spectrometry
   PCR
   sequencing
   On-column or in-line detection
   electrophoresis In another example it may be desirable to investigate the response of different cell types to a drug. For example, a known cancer drug effective on one cell type may also be effective on another cell type. The following experiment could be performed.
   Attach labelled drug to the column (or could attach cells)
   Add cancer cells of a different type
   Wash
   Elute
   Count/separate labelled cells in cell sorter As mentioned above, partitioning may be useful in some instances. For example, partitioning can be used to distinguish between several promising drug candidates, all of which bind the cells with relatively low affinity.
   Immobilize cells on a column
   Add mixture of several labelled drug candidates
   Collect fractions or use in-line detection In this experiment, the relative binding efficacy of each drug candidate is determined by its elution order. This technique can also be used to characterize the relative binding efficacy of different monoclonal antibodies. Cells can be immobilized on the column and challenged with different monoclonal antibodies. In some embodiments, a known drug might be tweaked for instance by mutagenesis or synthesis. The relative binding of different drug analogues could then be investigated using partitioning.

In another embodiment, the following experiment could be performed to simultaneously identify drug targets and drug leads.

1. Immobilize cell of choice on column
2. Screen DNA bar-coded small molecule drug libraries, antibodies or antibody derivatives
3. Present drug libraries to cell-immobilized columns
4. For a negative control, do not present drug libraries
5. Wash
6. Release negative control cells and cells in complex with drug leads
7. Disrupt negative control cells and cells in complex with drug leads to generate membrane fragments consisting of cell-surface proteins and cell surface proteins bound to drug leads
8. Run non-denaturing gels of negative control membrane fractions and experimental membrane fractions.
9. Identify, through gel shift, membrane protein-drug complexes.
10. Extract leads and use mass spec to identify membrane protein and drug lead.

In certain embodiments, cells can be immobilized on the column and displacement chromatography can be used. For example, it may be desirable to compete off a naturally-occurring ligand with a drug for a pathway blocking drug application.

Breakthrough or frontal chromatography can be used in some instances, particularly for drug maturation studies. Breakthrough curves such as the one shown in FIG. 13 can aid in identifying entities having the desired binding kinetics, regardless of whether they're fast or slow. Several drug candidates or analogues can be compared in this manner.

The use of columns is advantageous for sequential additions of different molecules or compounds. For example, to examine calcium-dependent interactions, calcium could be added to the cells immobilized on a column, followed by the addition of a library.

Liquid-Sealed Chromatographic System

The sealed chromatographic system is a liquid chromatography column that operates without exposure to ambient conditions. Ambient conditions are defined herein as the conditions of the surrounding environment. The sample, wash and elution solutions are passed through the column in a closed environment. The column can be sterile and can be used to isolate cells or enrich for cells in a sterile environment. The column itself and the solutions passed through the column can be sterile. The entire chromatographic process is performed under sealed or closed conditions including sample loading onto the column, column washing, and column elution. The purified product is recovered in a closed receiving container. The sealed format prevents contaminants from entering the system.

As with other embodiments described herein, cells can be captured using affinity, hydrophobic interaction, reverse phase, normal phase, ion pairing, ion exchange or other strategies. Alternatively, an enrichment can be performed in which the desired cell types pass through the column while other non-desired materials are retained.

Liquids flow from a feed bag or reservoir to a receiving bag/reservoir. Flow through the column can be bidirectional or unidirectional. Bidirectional or back and forth flow can optionally be used for any or all of the equilibration, capture, wash and elute processes.

Figure 14:
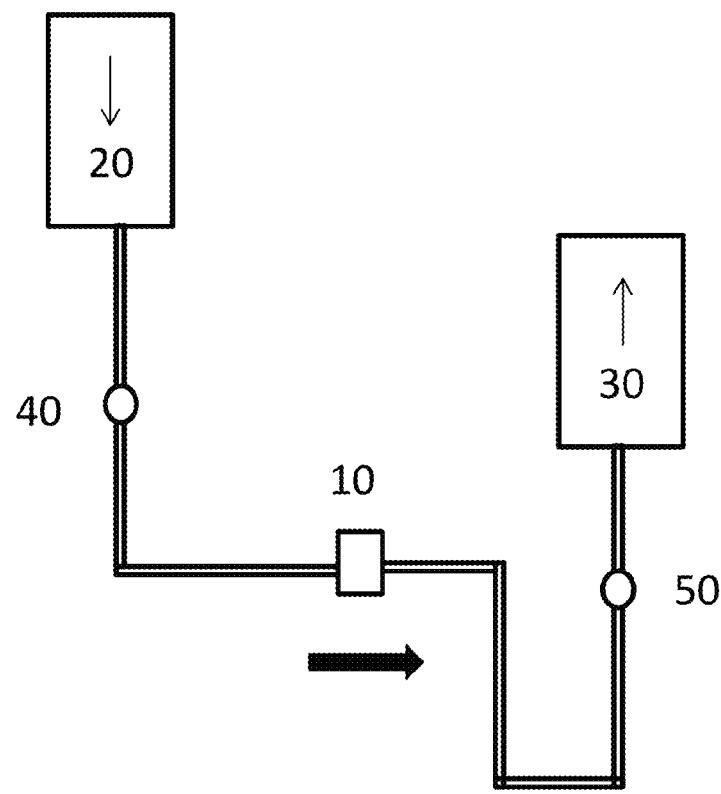
FIG. 14 depicts an embodiment of a closed column system for capture of cells with a back and forth flowing system.
Figure 14:
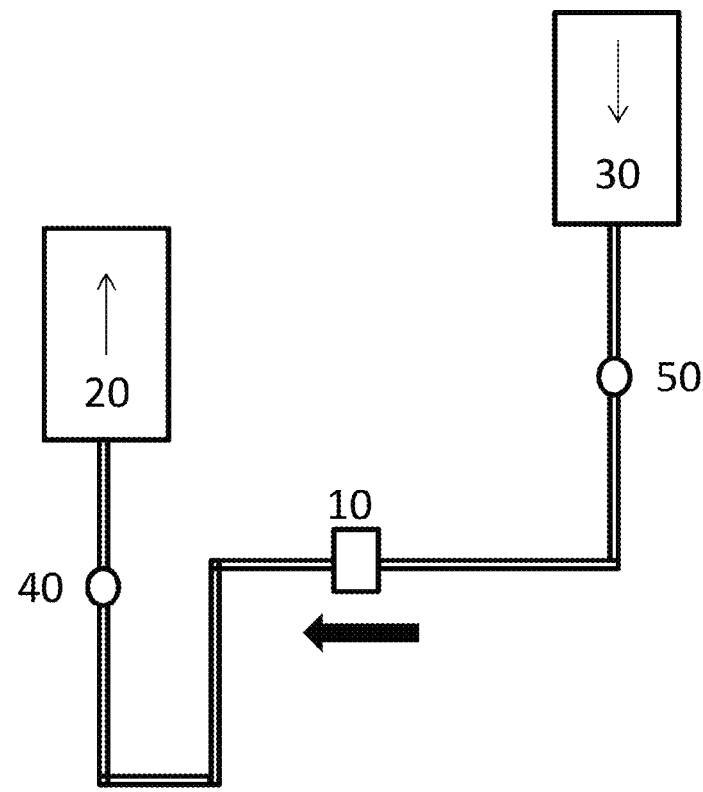

FIG. 14 shows an example of a sealed column system for cell capture with a back and forth flowing system. The flow is controlled by the relative differences in the height of the feed and receiving closed containers. The system contains column 10 and reservoirs, 20 and 30. Depending on the direction of flow, a given reservoir can either be a feed to column 10 or the reservoir can receive flow from column 10. In some embodiments, the sealed column system may also contain on/off valves 40 and 50 to allow flow or stop flow. Reservoirs 20 and 30 are connected to valves 40 and 50 and column 10 with flexible tubing 60.

The flow through the column, 10 can be controlled by several different options. In one method, the relative difference in height of feed and receiving sealed containers will apply a positive pressure on one side of the column and a negative pressure on the other side of the column. In FIG. 14A, reservoir 20 is positioned above column 10 and reservoir 30 is positioned lower than reservoir 20. This will cause flow from reservoir 20 through the column 10 and into reservoir 30 as depicted by the arrow below column 10. The flow rate can be increased by changing the relative position of the two reservoirs, for example by increasing the height of reservoir 20 or lowering reservoir 30. Reservoir 30 may be placed below column 10 or above the height of column 10.

Reversing the positions of the two reservoirs as shown in FIG. 14B will reverse the flow through column 10 as shown by the arrow going from right to left below the column. Flow will stop when the feed reservoir is depleted or the receiving reservoir is full.

In some embodiments, flow through sealed column 10 may be powered by peristaltic pumps. For example, valve 40 and/or 50 may be replaced with a peristaltic pump or pumps. When a peristaltic pump is used, the tubing can remain sealed. Flow through the sealed column may also be performed with syringe pumps. For example, reservoirs 20 and/or 30 can be replaced with syringe pumps. In this embodiment, feed and receiving chambers 20 and 30 remain sealed.

Figure 15:
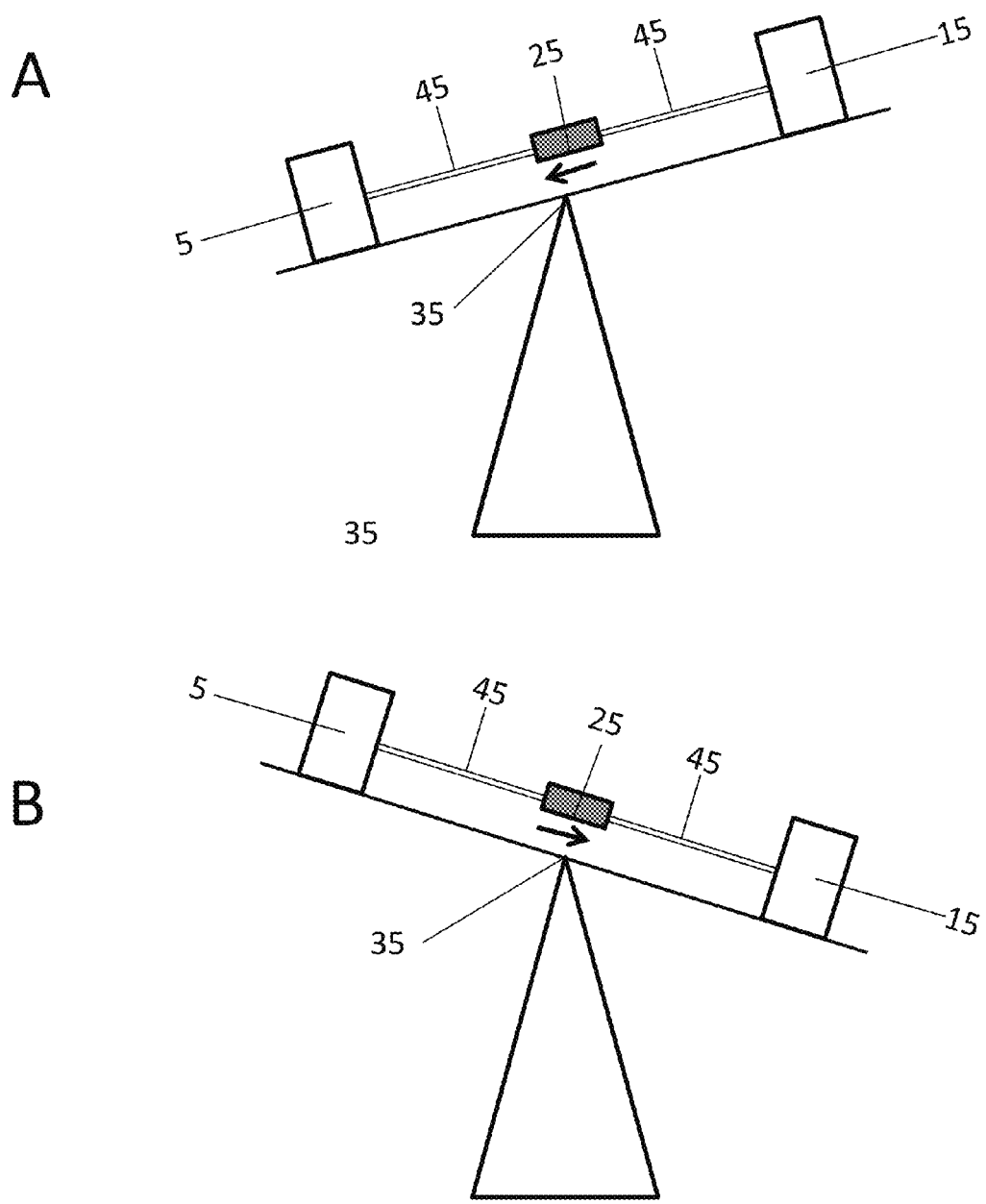
FIG. 15 depicts an embodiment of a closed column system for capture of cells with a back and forth flowing system with two feed and receiving containers on each side of the column.

FIG. 15 shows an alternate embodiment of a sealed column system for capture of cells with a back and forth flowing system. The system contains column 25 and reservoirs 5 and 15. Depending on the direction of flow, a given reservoir can either provide feed to column 25 or receive effluent flow from the column. The reservoirs are connected to the column through tubing which can be flexible sealed tubing. The flow through the column 25 is controlled by placing the reservoirs and column on platform 55 where fulcrum 35 is positioned at or near column 25. The reservoirs are raised and lowered relative to each other by tilting platform 55 at fulcrum 35.

The relative difference in height of the feed and receiving sealed containers will apply a positive pressure on one side of the column and negative pressure on the other side of the column. In some embodiments the positive pressure of the feed reservoir can be in the range of 5 psi, 4.5 psi, 4 psi, 3.5 psi, 3 psi, 2.5 psi, 2 psi, 1.5 psi, 1 psi, 0.5 psi, 0.25 psi, 0.1 psi, 0.01 psi or 0.001 psi. Likewise, the pressure in the receiving reservoir can be in the same range, however it is also possible for the pressure of in the receiving reservoir to be 0. Flow will stop when the feed reservoir is depleted or the receiving reservoir is full.

FIG. 16 depicts a sealed column system for capture of cells with a back and forth flowing system with two feed and receiving containers on each side of the column. The on/off valves control the flow into and out of a particular container.

Figure 17:
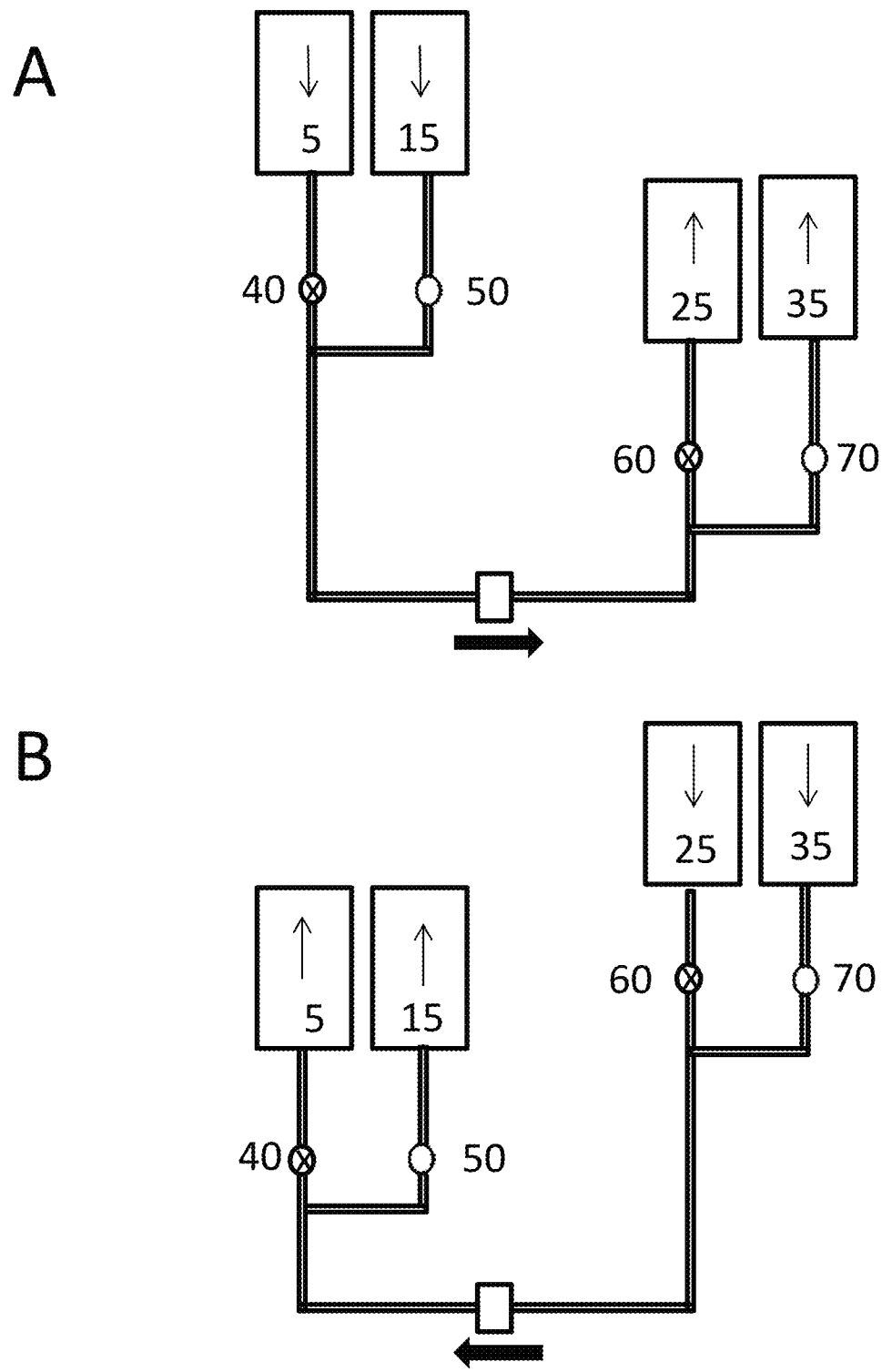
FIG. 17 depicts the same system as FIG. 16 in an alternate configuration.

In FIGS. 16A and 16B, valves 50 and 70 are closed and flow is between closed containers 15 and 35. FIGS. 17A and 17B depict the same system architecture in an alternate configuration in which valves 50 and 70 are open while valves 40 and 60 are closed.

Figure 18:
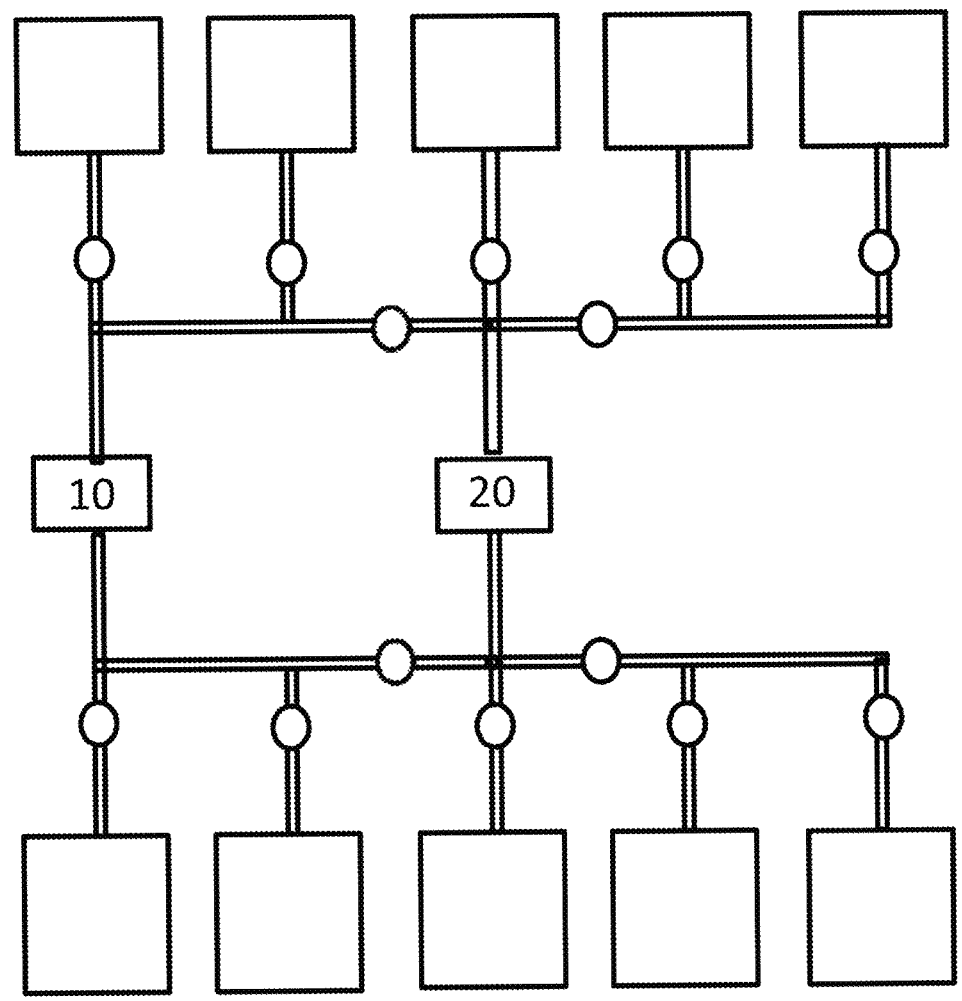
FIG. 18 depicts an alternative configuration of a sealed liquid chromatography column system.

FIG. 18 depicts an alternative configuration of a sealed liquid chromatography column system for capturing cells using a back and forth flowing system. In this configuration, there are two columns 10 and 20. Column 20 has five feed and receiving containers on each side of the column. The on/off valves control the feed and receiving container that is in use and the particular column that is used as described in FIG. 15. A specified purification, washing and recover method uses a controlled sequence of valves (pictured as small ovals) opening and closing. Second column 10 gives the option of using a second chemical treatment on purified and recovered cells from column 20. The sealed chromatography system is described in more detail below in Example 18.

In some embodiments, a manifold can be used to introduce other liquid into the column in a sealed system including wash and elution solutions. A third bag can be configured to receive purified cells. A second column can be configured to clean the purified cells for materials including antibodies, biotin, etc. with the cells received into a fourth bag. In some embodiments, the system can be used to remove cancer cells or pathogens from blood. In all cases, back and forth flow can be used if necessary to achieve a complete reaction process.

Pressures applied to the sealed chromatography system column and reservoirs are complex. The separation column has an additional backpressure or resistance to flow force exerted upon it. This is due to the eluent flowing out of the column which is in direct fluid contact with the reservoir of fluid collected from the column. The backpressure will change depending on the relative volumes of liquid above and below the columns (inlet and outlets) and the positions of the inlet and outlet volumes. It is not possible to predict the pressures as they are variable. It is surprising that that flow of fluids can be initiated (in either direction), maintained and established with the column configuration and design constraints. It is also surprising that the capture, washing and recovery of cells can be accomplished with variable flow rates and variable pressures. It is also surprising that the process can be performed reproducibly and predictably (predictable purity, concentration and volume).

In the sealed system, resistance of liquid and cell flow through the column is caused not only by the column but also by the receiving container which is in intimate contact with the fluid. A positive pressure is needed to expand the receiving container as it is filled from the column effluent. There may also be a pressure pushing back against or resisting the flow caused by the receiving container attempting to contract rather than expand. This resistance to flow through the column is in addition of the liquid attempting to flow through the column and the cells themselves having a resistance of traversing the column. Thus, the positive force needed to pump the cells and liquid through the column must overcome all of these forces in a sealed system. The positive force pushing the liquid through the column will be variable and, if gravity is used, will become exceedingly small, as the amount of liquid on top of the column approaches zero force with depletion of the liquid above the column. Nevertheless, all of the liquid can be pumped through the column.

Non-limiting examples of the ways in which the columns and methods of the invention can be used include the following.

1) capture and release of cells
2) depletion of cells from a complex mixture and retention of remaining cells
3) capture labeled cells, then release and count
4) Capture cells, lyse cells on column or after the cells have been eluted from the column. Collect DNA, RNA or proteins or other cellular components and analyze.
5) Purify sperm from other cells or from the environment.
6) Purify sperm from a crime scene away from other cells and other materials and perform DNA analysis to identify the source of the sperm
7) After cell capture, the column is washed and cells can optionally be reacted with a dye to label the captured cells. The resin may be removed from the column and plated or spread on a surface. The resin beads containing attached cells may be sorted and counted or analyzed by any means.
8) Capture a group or class of cells based on a specific parameter and then perform a secondary capture step to produce and recover a subset of cells.
9) Capture and recover cells from blood, fluid, marrow, skin and tissue.
10) Capture and recovery of live cells from the examples listed above from various samples including, blood, fluid, marrow, skin and tissue.
11) Capture and recovery of cells. Cells are then used for therapeutic purpose.
12) Capture and recovery of large amount of cells on a pipette tip column having a body size in the range of 2 mL-100 mL.
13) Therapeutics screening
14) Cell clean-up
15) Diagnostics

EXAMPLES

Example 1

Sperm is Captured, Separated from Cells and DNA Analysis is Performed

In forensics, it is often desired to obtain DNA profiles from old stains, body fluid samples and other possible samples. The primary goal is to preferentially separate sperm from vaginal cells and other materials, a necessity for DNA analysis in rape cases, for example.

DNA aptamers which are short strands of DNA were developed by SomaLogic (Denver, Colo.) to bind sperm heads, and used to both identify and immobilize the sperm heads for purification and later DNA analysis. These aptamers are used in a column bed system of the invention with Biotin and Streptavidin linkers to selectively capture sperm cells. The aptamer sequences bind preferentially to both the outer protein membrane and the stripped perinuclear calyx of sperm cells in the presence of non-sperm epithelial cells.

Sperm cells (research vials, prepared by density gradient centrifugation and subsequent washing) are purchased from California Cryobank. Washed sperm cells are prepared using three washes and suspension in a buffer supplemented with Triton X100 detergent and NaCl to final concentrations of 1% v/v and 600 mM HeLa cells to simulate non-sperm epithelial cells are added and the mixtures are incubated for ten minutes.

Cotton swabs are used to simulate capturing the sperm sample. The sample is removed from the cotton swab with a buffer. Aptamers with biotin linkers are added to the solution and incubated. After washing of the sample the mixture is passed through a streptavidin packed bed column of the invention. The sperm is captured and subsequently washed by passing wash buffer through the column.

The sperm is eluted from the column by passing a buffer through the column breaking up the aptamer/sperm column. Eluted aptamer DNA are purified and then amplified for DNA analysis.

Example 2

Antibody Purification of Sperm

This example uses antibodies rather than aptamers to capture sperm cells in the presence of other cells. A cocktail of antibodies specific to sperm cell surface antigens are anchored to Protein A affinity beads packed into a column of the invention. The specificity of antibody-antigen binding selectively captures sperm cells from samples that are comprised of a mixture of sperm cells, white blood cells, epithelial cells, cell lysates, etc. Alternatively, the antibodies are added to the sample mixture first and then captured by the column. After washing with a neutral buffer, the sperm cells are eluted with low pH or high pH buffers and the DNA is analyzed.

The antibodies may be tagged with His tags for example. In this case, IMAC beads may be packed into columns of the invention to capture the antibodies which are used in turn, to capture the sperm. In this case, the antibody sperm combination may be eluted, the cell lysed and the DNA analyzed. Other tags may be used such as FLAG-ANTIFLAG, etc.

Peptide tags are used for capture. These include AviTag, a peptide allowing biotinylation by the enzyme BirA so the protein can be isolated by streptavidin, Calmodulin-tag, a peptide bound by the protein calmodulin, FLAG-tag, a peptide recognized by an antibody, HA-tag, a peptide recognized by an antibody, Myc-tag, a short peptide recognized by an antibody, SBP-tag, a peptide which binds to streptavidin, Softag 1, for mammalian expression, Softag 3, for prokaryotic expression, V5 tag, a peptide recognized by an antibody, and Xpress tag.

Covalent tags include Isopeptag which binds covalently to pilin-C protein and SpyTag which binds covalently to SpyCatcher protein.

Protein tags include BCCP (Biotin Carboxyl Carrier Protein), a protein domain recognized by streptavidin, glutathione-S-transferase-tag, a protein which binds to immobilized glutathione, green fluorescent protein-tag, a protein which is spontaneously fluorescent and can be bound by nanobodies, maltose binding protein-tag, a protein which binds to amylose agarose, Nus-tag, Strep-tag, a peptide which binds to streptavidin or the modified streptavidin called Strep-Tactin and Thioredoxin-tag.

Example 3

Circulating Tumor Cells

A cancerous tumor sheds small numbers of tumorous cells into its immediate vasculature. These cells then make their way into the circulatory system, and are thus called circulating tumor cells (CTCs). CTC information is used cancer prognosis, therapy monitoring and metastasis research.

Circulating tumor cells (CTCs) are important targets for study to understand, diagnose, and treat cancers. However, CTCs are found in blood at extremely low concentrations which makes isolation, enrichment and characterization challenging. A typical concentration in a human cancer patient is approximately 1-100 CTCs per mL of blood.

CTC purification with the columns of the invention capture many or most of the CTCs in the blood sample (high capture efficiency) and are selective with very few other cells accidently isolated. The samples are processed with sufficient speed and without battering of the cells so that cells remain viable in many cases.

The columns of the invention operate by coating the column media with an antibody (anti-EpCAM) and then bonding the antibody to the epithelial adhesion molecules (EpCAM) of CTCs. After capture of anti-EpCAM labeled CTCs from a blood sample, CTC identification and enumeration are achieved using immunostaining.

During one experiment 2 to 80 spiked breast cancer cells are isolated from 1 mL of mice blood sample with 90% capture efficiency. A 200 µL bed column with a 1 mL pipette tip body is used for one experiment. Whole blood is processed through the column with bidirectional flow for 5 cycles at 200 uL/min flow rate. The column is washed with buffer and then the cells are eluted with 500 mM citric acid.

Example 4

Capture of Cells from Blood

The purification and analysis processes used in example 3 are used for other cell types including white blood cells, stem cells, T cells, B cells and others. In this example, the medium used can be capable of capturing each cell type. Alternatively, the medium may capture other sample components, thereby enriching for the desired cell type.

Example 5

Capture of Cells from Blood

The purification and analysis processes used in examples 3 and 4 are used except the pumping methods for flowing the fluids through the column are changed as follows. The pumping method is bidirectional, unidirectional, gravity flow and gravity flow plus vacuum and/or pressure.

In addition, the method is performed with two different column configurations. In one configuration, there is an air gap above the column bed, while in the other configuration, there is no air gap above the column bed.

Example 6

Capture of Cells from Blood

The purification and analysis processes used in examples 3, 4 and 5 are used except the column has a bed volume of 1 mL inside a 10 mL pipette body. The flow rates are approximately 10 times faster with this column so samples sizes approximately 10 times greater are processed in approximately the same time.

In this example the cells are released from the column by enzymatic and chemical cleavage of the linker. The cells are collected and counted.

Examples 7

Capture of Cells from Tissue

For tissue samples composed of different types of cells, heterogeneous cell populations will be present. To obtain as much information as possible about an individual cell type, biologists have developed ways of dissociating cells from tissues and separating the various types. A mild procedure is used to collect whole, intact cells. Homogenized cells are kept at low temperatures to prevent autolysis and kept in an isotonic solution to prevent osmotic damage.

The first step in isolating cells of a uniform type from a tissue that contains a mixture of cell types is to disrupt the extracellular matrix that holds the cells together. For example, viable dissociated cells are obtained from fetal or neonatal tissues. The tissue sample is treated with proteolytic enzymes (such as trypsin and collagenase) to digest proteins in the extracellular matrix and with agents (such as ethylenediaminetetraacetic acid, or EDTA) that bind, or chelate, the $Ca^{2+}$ on which cell-cell adhesion depends. The tissue can then be teased apart into single living cells by gentle agitation to make a cell suspension.

Columns of the inventions are loaded with antibodies that have an affinity for fetal cells. The suspension is passed with bidirectional flow through the column to capture the cells. After washing, the cells are released with by treatment with trypsin to digest the antibodies. The cells may be visually tagged by using an antibody coupled to a fluorescent dye to label specific cells.

Given appropriate surroundings, most plant and animal cells can live, multiply, and even express differentiated properties in a tissue-culture dish. The cells can be watched continuously under the microscope or analyzed biochemically, and the effects of adding or removing specific molecules, such as hormones or growth factors, can be explored. In addition, by mixing two cell types, the interactions between one cell type and another can be studied. Experiments performed on cultured cells are sometimes said to be carried out in vitro (literally, "in glass") to contrast them with experiments using intact organisms, which are said to be carried out in vivo (literally, "in the living organism"). These terms can be confusing, however, because they are often used in a very different sense by biochemists. In the biochemistry lab, in vitro refers to reactions carried out in a test tube in the absence of living cells, whereas in vivo refers to any reaction taking place inside a living cell (even cells that are growing in culture).

Example 8

Capture of Bacterial Cells

An *E. coli* culture is grown at 37° C. The *E. coli* strain is engineered using recombinant DNA techniques so that surface proteins on the cell contain histidine tags. A spike of Salmonella is added to the sample so that the sample contains 10% Salmonella cells, 90% *E. coli* cells, media and other materials.

A 1 mL bed size column containing Ni form IMAC affinity media is used to treat or process a 3 mL sample with unidirectional single pass flow under gravity. Some air pressure is used to push the last remaining solution through the column. The *E. coli* cells are removed from the mixture and are captured on the column while the Salmonella cells remain in the sample.

Example 9

Capture of Cells from Culture

Most plant and animal cells can live, multiply, and even express differentiated properties in a tissue-culture dish. The cells can be watched continuously under the microscope or analyzed biochemically, and the effects of adding or removing specific molecules, such as hormones or growth factors can be explored. In addition, by mixing two cell types, the interactions between one cell type and another can be studied. After growing the cells, the specific cells are captured according to processes similar to those described in examples 7 and 8.

After capture, the column is washed and optionally reacted with a dye to label the captured cells. The resin may be removed from the column and plated or spread on a surface. The resin beads containing attached cells may be sorted and counted or analyzed by any means.

Example 10

Companion Diagnostic to Antibody or FAB Based Drug

Often it is unknown whether a particular antibody or FAB drug will be effective against a particular cancer case. The treatment process can be trial and error, trying one drug and then if it is not effective, trying the next drug and so on. Columns of the invention may be used to determine the potential effectiveness of a series of drugs. Tagged drug antibodies and FABs are prepared. A series of columns of the invention are prepared each with a single antibody bound through the tag to the media of the column. In this way, each available drug is represented by a column. Then a blood sample from a cancer patient is treated by the series of columns in an attempt to capture circulating tumor cells. The columns are washed and the cells, if present, are recovered and analyzed by fluorescence, DNA, microscopy or any suitable analytical technology. Specific drugs that may be effective against the cancer are captured containing drug based affinity media. Then a treatment program is designed using the antibody/FAB drugs that have the highest affinity for the tumor.

Example 11

Nickel-IMAC Column Sterilization 1-ml pipette tip columns containing 80 µL of Ni-IMAC resin were manufactured and 100% glycerol was added to the columns so that the glycerol filled the resin bed up to several millimeters above the bed. The columns were placed in a pipette tip box and the box was autoclaved at 132° C. for 45 minutes.

To verify column sterility, the column resin and a piece of the column body were placed on an LB plate and the plate was incubated at 37° C. After 3 days, no bacterial growth was evident.

The performance of the autoclaved columns was compared with identical columns that had not been autoclaved. His-tagged enhanced green fluorescent protein (eGFP) was purified on the columns using an E4 XLS pipette (Rainin) as shown in Table 1.

After the sample was loaded onto the columns, two washes were performed. The column was washed with 10 mM $NaH_2PO_4$, 5 mM Imidazole, 0.3 M NaCl, pH 7.4 followed by 10 mM $NaH_2PO_4$, 0.3 M NaCl, 20 mM Imidazole, pH 7.4. Next the eGFP was eluted with 10 mM $NaH_2PO_4$, 0.14M NaCl, 0.25M Imidazole, pH 7.4.

TABLE 1

| E4 XLS pipette settings: | | | |
|---|---|---|---|
| | Volume mL | Cycles | Speed |
| Equilibration | 0.50 | 1 | Medium |
| Sample | 0.50 | 4 | Medium |
| Wash 1 | 0.50 | 2 | Medium |
| Wash 2 | 0.50 | 2 | Medium |
| Elute | 0.24 | 4 | Medium |

The absorbance of the eluate was read at 488 nm and the yield of purified eGFP was determined. Both the autoclaved column and the column that had not been autoclaved were able to capture eGFP as shown in Table 2 below.

TABLE 2

Columns 1 and 2 were autoclaved and columns 3 and 4 were not autoclaved.

| Column | eGFP excitation peak | Absorbance | Concentration mg/mL | Volume mL | Yield mg |
|---|---|---|---|---|---|
| 1 | 488 | 0.075 | 0.331 | 0.733 | 0.242 |
| 2 | 488 | 0.074 | 0.326 | 0.741 | 0.242 |
| 3 | 488 | 0.081 | 0.357 | 0.753 | 0.269 |
| 4 | 488 | 0.079 | 0.348 | 0.740 | 0.258 |

Example 12

Protein-A Column Sterilization 1-ml pipette tip columns containing 80 µL of proA resin (PhyNexus, Inc.) were placed in a pipette tip box and the box was autoclaved at 132° C. for 45 minutes. Some of the columns contained glycerol while others did not.

To verify column sterility, the column resin and a piece of the column body were placed on an LB plate and the plate was incubated at 37° C. After 3 days, no bacterial growth was evident.

IgG was loaded on the columns and the columns were operated with an E4 XLS pipette (Rainin) as shown above in Table 1. After the sample was loaded, the columns were washed with phosphate buffered saline (Wash 1) and 140 mM NaCl (Wash 2). The protein was eluted with 200 mM $PO_4$, 140 mM NaCl @ pH 2.5.

The protein yield from the autoclaved columns was compared with the yield obtained from identical columns that had not been autoclaved. The yield of purified IgG obtained the autoclaved proA columns was comparable to those columns that had not been autoclaved.

Example 13

Column Sterilization

Four, 1-ml pipette tip columns containing 80 µL of agarose resin were autoclaved at 132° C. for 45 minutes. Two different agarose resins were used; agarose 1 and agarose 2. Prior to autoclaving, glycerol was added to one column of each resin type. After autoclaving, it was observed that the resin dried out in the columns that did not contain glycerol while the two columns with glycerol added remained wet as shown in Table 3.

TABLE 3

| Column sterilization | | | |
|---|---|---|---|
| Resin | Glycerol | Autoclaved | Dried Out |
| Agarose1 | No | Yes | Yes |
| Agarose1 | Yes | Yes | No |
| Agarose2 | No | Yes | Yes |
| Agarose2 | Yes | Yes | No |

Example 14

Negative Isolation of Stem Cells

In this example, a sample is enriched for stem cells by removing other cell types. A column is assembled in which the medium is comprised of antibodies that bind undesired cells. The sample is loaded onto the column and the undesired cells are captured on the column. The column flow-through is collected and shown to be enriched for the desired cells.

Example 15

Negative Selection of T Cells from Peripheral Blood Mononuclear Cells

T cells are isolated by depletion of all non-T cells such as B cells, macrophages, and natural killer cells. Peripheral blood mononuclear cells (PBMC) are incubated with a mixture of monoclonal antibodies to coat unwanted cells. The suspensions are then loaded onto a column comprised of IgG, which binds the antibody-coated cells. The column flow-through is collected and shown to be enriched for the T cells.

Example 16

Negative Selection of T Cells

The method from Example 15 is applied to different samples such as cells from spleen, lymph node, tumor, and peritoneal fluid.

Example 17

Purification of Sperm Cells by Aptamer Binding

An RNA aptamer having the following sequence is synthesized. Ggcagtccgt ccgtcAZCGA CGCGZGZGZG ZZZGZCZZCZ ZGZZZGZZGZ CGZGCgccag aagcagaagg acg Z is the modified base, 5-(N-benzylcarboxyamide)-2'-deoxyuridine. A photocleavable linker is conjugated in between the beads and the aptamer to elute the bound cells from the RNA aptamer in one step by UV irradiation The synthesized aptamer is incubated with streptavidin beads in a 1 ml pipette-tip column containing 80 µl of streptavidin resin. A 1 ml sample comprised of sperm cells mixed with other cells is eluted from a swab obtained from sexual assault evidence and diluted in 40 mM Hepes pH 7.5, 350 mM NaCl, 1 mM EDTA, 0.5 mM EGTA, and 0.1% Triton X100 detergent.

The sample is aspirated and expelled from the pipette tip column three times at a rate of 150 µl/min. Non-specifically bound material is removed from the column by washing the column three times with 1 ml of 40 mM Hepes pH 7.5, 350 mM NaCl, 1 mM EDTA, 0.5 mM EGTA, and 0.1% Triton X100. To cleave the aptamer and cells from the resin, the column is subjected to UV irradiation at 1050 mW/cm2 for 5 min. The cells are eluted by aspirating and expelling two times with 500 µl of 40 mM Hepes pH 7.5, 350 mM NaCl, 1 mM EDTA, 0.5 mM EGTA, and 0.1% Triton X100 detergent.

Example 18

A Closed Chromatograph System

A column was assembled by gluing a frit on one end, packing the column and then gluing the frit on the top of the column. A 37 micron pore, 60 micron thick Nitex screen frits was attached to the end of an acrylic tube 0.750 inches long, 0.500 inch outer diameter and 0.375 inch inner diameter. The tube with frit side down was placed on a deep well plate for packing. Packing was accomplished by standing the column on a stand with hole beneath that allowed the flow of liquid out of the lower end. An aqueous slurry of agarose resin, 45-165 micron particle size, was placed into the column by pipette. The packing material was not compressed. Excess liquid drained away filling the column with resin. Additional slurry was added until the bed of the column reached the top of the column. The end frit of a Nitex screen of the same material was glued onto the column end using a methylene chloride solvent.

Silicone tape was wrapped round the column to increase the diameter. Then two 10-mL plastic syringe bodies and male luer connections were cut to the 1 mL volume mark and placed on the end of the column. The column body was wrapped with stretchable silicone tape to seal the column body.

Male luer connections were connected to the inside of clear flexible Tygon tubing 0.25 inch outer diameter with pinch valve. The tubing was connected to 1000 mL Kendall cat no 763656 adapted to be a flexible closed feed/receiving bag containers. 250 mL of DI water was added to one of the containers and sealed. At this point, no air remained in the system and the entire column and receiver/feed system was closed to the outside.

The feed bag was filled with 250 mL of DI water with the tube pinch valve pinched closed and placed on a stand. The receiving bag was placed on stand 10 inches below the feed bad. The pinch valve was opened and the fluid flowed from the feed bag through the feed bag into the receiving bag in a closed system. Flow was controlled by the relative difference in height of the two bag containers. Flow as low as a couple of µL/min was employed to as high as 20 mL/min for this particular column. Higher flow rates are possible with greater height differences, lower backpressure columns or the use of peristaltic or bag compression pumping.

After the flow through the column was completed, the relative position of the feed bag and receiving bag was reversed by simply lowering the feed bag (now the receiving bag) and raising the receiving bag (now the feed bag), reversing the flow through the column. This can process can be performed as often as necessary to provide complete capture of the cell or other process.

The invention claimed is:
1. A method for capturing cells in a liquid-sealed chromatographic column system, comprising the steps of:
 (a) providing a liquid-sealed column system, wherein the system is comprised of
  (i) a column having a first end and a second end, wherein the column contains a solid phase, wherein the solid phase is capable of cell capture,
  (ii) at least two reservoirs, wherein there is a first reservoir and a second reservoir, wherein the first reservoir contains a sample solution comprised of cells, wherein the first reservoir can serve as a feed reservoir or a receiving reservoir, and wherein the second reservoir can serve as the feed reservoir or the receiving reservoir,
  (iii) a first length of tubing, wherein the first length of tubing connects the first end of the column to the first reservoir,
  (iv) a second length of tubing, wherein the second length of tubing connects the second end of the column to the second reservoir;
 (b) passing the sample solution in a first direction, wherein the sample solution is passed from the first reservoir through the column into the second reservoir, whereby at least some of the cells are captured on the solid phase of the column; and
 (c) passing the sample solution in a second direction, wherein the sample solution is passed from the second reservoir through the column into the first reservoir, wherein the first direction and the second direction are opposite directions.

2. The method of claim 1, wherein the column contains a packed bed.

3. The method of claim 1, wherein the solid phase is comprised of an affinity group that binds cells.

4. The method of claim 1, the wherein the feed reservoir is higher than the receiving reservoir and the sample solution is passed through the column using gravity flow.

5. The method of claim 4, wherein the feed reservoir has a positive pressure of less than 5 psi and wherein the receiving reservoir has a backpressure of less than 5 psi.

6. The method of claim 1, wherein the liquid-sealed chromatographic column system is sterile.

7. The method of claim 1, wherein the liquid-sealed chromatographic column system is further comprised of valves.

8. The method of claim 7, wherein the liquid-sealed chromatographic column system is further comprised of at least one peristaltic pump attached to the liquid-sealed system, and wherein liquid is passed through the column by pumping.

9. The method of claim 7, wherein the liquid-sealed chromatographic column system is comprised of two feed reservoirs and two receiving reservoirs.

10. The method of claim 7, wherein the liquid-sealed chromatographic column system is comprised of three feed reservoirs and three receiving reservoirs.

11. A method for enriching a sample in a liquid-sealed chromatographic column system, comprising the steps of:
 (a) providing a liquid-sealed chromatographic column system, wherein the system is comprised of
  (i) a column having a first end and a second end, wherein the column contains a solid phase,
  (ii) at least two reservoirs, wherein there is a first reservoir and a second reservoir, wherein the first reservoir contains a sample solution comprised of cells and undesired material, wherein the first reservoir can serve as a feed reservoir or a receiving reservoir, and wherein the second reservoir can serve as the feed reservoir or the receiving reservoir, (iii) a first length of tubing, wherein the first length of tubing connects the first end of the column to the first reservoir, (iv) a second length of tubing, wherein the second length of tubing connects the second end of the column to the second reservoir;

(b) passing the sample solution in a first direction, wherein the sample solution is passed from the first reservoir through the column into the second reservoir, whereby the cells pass through the column and the undesired material is captured on the solid phase of the column; and (c) passing the sample solution in a second direction, wherein the sample solution is passed from the second reservoir through the column into the first reservoir, wherein the first direction and the second direction are opposite directions.

12. The method of claim 11, wherein the column contains a packed bed.

13. The method of claim 11, wherein the solid phase is comprised of an affinity group that binds undesired material.

14. The method of claim 11, the wherein the feed reservoir is higher than the receiving reservoir and the sample solution is passed through the column using gravity flow.

15. The method of claim 14, wherein the feed reservoir has a positive pressure of less than 5 psi and wherein the receiving reservoir has a backpressure of less than 5 psi.

16. The method of claim 14, wherein the liquid-sealed chromatographic column system is sterile.

17. The method of claim 11, wherein the liquid-sealed chromatographic column system is further comprised of valves.

18. The method of claim 17, wherein the liquid-sealed chromatographic column system is further comprised of at least one peristaltic pump, wherein liquid is passed through the column by pumping.

19. The method of claim 17, wherein the liquid-sealed chromatographic column system is comprised of two feed reservoirs and two receiving reservoirs.

20. The method of claim 17, wherein the liquid-sealed chromatographic column system is comprised of three feed reservoirs and three receiving reservoirs.

21. A method for capturing cells in a liquid-sealed chromatographic column system, comprising the steps of:

(a) providing a liquid-sealed chromatographic system comprised of (i) a column having a first end and a second end, wherein the column contains a solid phase capable of cell capture, (ii) at least two reservoirs attached to the first end of the column, at least a first reservoir attached to the first end of the column, a second reservoir attached to the first end of the column and optionally, a third reservoir attached to the first end of the column, wherein each reservoir contains a solution selected from the group consisting of a sample solution, a wash solution and an eluent, wherein each reservoir can serve as a feed reservoir and a receiving reservoir, wherein each reservoir is attached to the column by a length of tubing, wherein each length of tubing is further comprised of a valve, (iii) at least two reservoirs attached to the second end of the column, at least a first reservoir attached to the second end of the column, a second reservoir attached to the second end of the column and optionally, a third reservoir attached to the second end of the column, wherein the reservoirs attached to the second end of the column can serve as feed reservoirs or receiving reservoirs, wherein each reservoir is attached to the column by a length of tubing, wherein each length of tubing is further comprised of a valve;

(b) passing the sample solution in a first direction, wherein the sample solution is passed from the first reservoir attached to the first end of the column through the column into the first reservoir attached to the second end of the column, whereby at least some of the cells are captured on the solid phase of the column;

(c) passing the sample solution in a second direction, wherein the sample solution is passed from the first reservoir attached to the second end of the column through the column into the first reservoir attached to the first end of the column, wherein the first direction and the second direction are opposite directions;

(d) optionally, repeating steps (b) and (c);

(e) passing a second solution in a first direction, wherein the second solution is selected from the group consisting of a sample solution, a wash solution and an eluent, wherein the second solution is passed from the second reservoir attached to the first end of the column through the column into the second reservoir attached to the second end of the column;

(f) optionally, passing the second solution in a second direction, wherein the second solution is passed from the second reservoir attached to the second end of the column through the column into the second reservoir attached to the first end of the column; and (g) optionally, repeating steps (e) and (f) with a third solution, wherein the third solution is selected from the group consisting of a sample solution, a wash solution and an eluent.

22. The method of claim 21, where in the liquid-sealed chromatographic column system is further comprised of at least one pump.

* * * * *